(12) United States Patent
Kimmel et al.

(10) Patent No.: US 9,757,538 B2
(45) Date of Patent: *Sep. 12, 2017

(54) MRI COMPATIBLE CONTROL HANDLE FOR STEERABLE SHEATH WITH AUDIBLE, TACTILE AND/OR VISUAL MEANS

(71) Applicant: IMRICOR MEDICAL SYSTEMS, INC., Burnsville, MN (US)

(72) Inventors: Scott Kimmel, Roseville, MN (US); Douglas A. Page, Apple Valley, MN (US)

(73) Assignee: IMRICOR MEDICAL SYSTEMS, INC., Burnsville, MN (US)

( * ) Notice: Subject to any disclaimer, the term of this patent is extended or adjusted under 35 U.S.C. 154(b) by 195 days.

This patent is subject to a terminal disclaimer.

(21) Appl. No.: 14/844,698

(22) Filed: Sep. 3, 2015

(65) Prior Publication Data

US 2016/0058975 A1    Mar. 3, 2016

Related U.S. Application Data

(63) Continuation-in-part of application No. 14/106,177, filed on Dec. 13, 2013, now Pat. No. 9,138,561, (Continued)

(51) Int. Cl.
*A61M 25/01* (2006.01)
*A61M 25/00* (2006.01)
*G01R 33/28* (2006.01)

(52) U.S. Cl.
CPC .... *A61M 25/0136* (2013.01); *A61M 25/0127* (2013.01); *A61M 25/0147* (2013.01);
(Continued)

(58) Field of Classification Search
CPC ............. A61B 5/05; A61M 5/00; A61M 5/32; A61M 31/00; A61M 29/00
(Continued)

(56) References Cited

U.S. PATENT DOCUMENTS 5,364,351 A    11/1994  Heinzelman et al.
5,507,725 A     4/1996  Savage et al.
(Continued)

FOREIGN PATENT DOCUMENTS

DE        69333140 T2      6/2004
DE     102011121964 A1     6/2013
(Continued)

OTHER PUBLICATIONS

Supplemental European Search Report and Opinion, issued by the European Patent Office, regarding corresponding patent application Serial No. EP 13862105.7; dated Nov. 18, 2016; 8 pages. EPO.
(Continued)

*Primary Examiner* — William Thomson
*Assistant Examiner* — Victor Shapiro
(74) *Attorney, Agent, or Firm* — Fox Rothschild LLP

(57) ABSTRACT

An MR compatible steerable sheath is provided. The MR compatible steerable sheath includes a steerable shaft that receives first and second longitudinal movement wires at a distal end thereof and audible or tactile means for indicating to a user the degree of deflection of the distal tip of the steerable shaft. A control handle is coupled to a proximal end of the first and second longitudinal movement wires and causes longitudinal movement of the wires.

23 Claims, 21 Drawing Sheets

Related U.S. Application Data which is a continuation-in-part of application No. 13/819,981, filed as application No. PCT/US2012/069487 on Dec. 13, 2012, now abandoned, said application No. 14/106,177 is a continuation of application No. PCT/US2013/074331, filed on Dec. 11, 2013.

(60) Provisional application No. 62/155,100, filed on Apr. 30, 2015, provisional application No. 61/576,161, filed on Dec. 15, 2011.

(52) U.S. Cl.
 CPC ..... *A61M 25/0052* (2013.01); *A61M 25/0054* (2013.01); *A61M 25/0108* (2013.01); *G01R 33/286* (2013.01)

(58) Field of Classification Search
 USPC .......... 604/8, 103; 600/410, 411; 606/1, 194
 See application file for complete search history.

(56) References Cited

U.S. PATENT DOCUMENTS

| | | | |
|---|---|---|---|
| 5,531,664 A | 7/1996 | Adachi et al. | |
| 5,545,200 A | 8/1996 | West et al. | |
| 5,603,697 A | 2/1997 | Grundy et al. | |
| 5,656,029 A | 8/1997 | Imran et al. | |
| 5,715,817 A | 2/1998 | Stevens-Wright et al. | |
| 5,735,795 A | 4/1998 | Young et al. | |
| 5,759,173 A | 6/1998 | Preissman et al. | |
| 5,826,576 A | 10/1998 | West | |
| 5,897,529 A | 4/1999 | Ponzi | |
| 5,906,590 A | 5/1999 | Hunjan et al. | |
| 5,938,616 A | 8/1999 | Eaton et al. | |
| 6,022,319 A | 2/2000 | Willard et al. | |
| 6,030,360 A | 2/2000 | Biggs | |
| 6,123,699 A | 9/2000 | Webster, Jr. | |
| 6,126,654 A | 10/2000 | Giba et al. | |
| 6,183,435 B1 | 2/2001 | Bumbalough et al. | |
| 6,251,092 B1 | 6/2001 | Qin et al. | |
| 6,261,255 B1 | 7/2001 | Mullis et al. | |
| 6,267,746 B1 | 7/2001 | Bumbalough | |
| 6,458,088 B1 | 10/2002 | Hurtak et al. | |
| 6,485,455 B1 | 11/2002 | Thompson et al. | |
| 6,551,271 B2 | 4/2003 | Nguyen | |
| 6,579,278 B1 | 6/2003 | Bencini | |
| 6,582,536 B2 | 6/2003 | Shimada | |
| 6,589,226 B1 | 7/2003 | Owens | |
| 6,611,720 B2 | 8/2003 | Hata et al. | |
| 6,620,150 B2 | 9/2003 | Kiemeneij | |
| 6,858,024 B1 | 2/2005 | Berg et al. | |
| 6,945,956 B2 | 9/2005 | Waldhauser et al. | |
| 6,976,987 B2 | 12/2005 | Flores | |
| 7,048,711 B2 | 5/2006 | Rosenman et al. | |
| 7,056,314 B1 | 6/2006 | Florio et al. | |
| 7,171,275 B2 | 1/2007 | Hata et al. | |
| 7,344,515 B2 | 3/2008 | Coyle | |
| 7,377,906 B2 | 5/2008 | Selkee | |
| 7,402,151 B2 | 7/2008 | Rosenman et al. | |
| 7,465,288 B2 | 12/2008 | Dudney et al. | |
| 7,591,784 B2 | 9/2009 | Butler | |
| 7,596,402 B2 | 9/2009 | Duerk et al. | |
| 7,606,609 B2 | 10/2009 | Muranushi et al. | |
| 7,615,044 B2 | 11/2009 | Scheibe et al. | |
| 7,682,319 B2 | 3/2010 | Martin et al. | |
| 7,682,358 B2 | 3/2010 | Gullickson et al. | |
| 7,691,095 B2 | 4/2010 | Bednarek et al. | |
| 7,803,130 B2 | 9/2010 | Ryan et al. | |
| 7,850,811 B2 | 12/2010 | Hart et al. | |
| 7,912,531 B1 | 3/2011 | Chiu et al. | |
| 7,955,305 B2 | 6/2011 | Moberg et al. | |
| 7,972,323 B1 | 7/2011 | Bencini et al. | |
| 8,016,784 B1 | 9/2011 | Hayzelden et al. | |
| 8,043,288 B2 | 10/2011 | Dando et al. | |
| 8,075,476 B2 | 12/2011 | Vargas | |
| 8,096,985 B2 | 1/2012 | Legaspi et al. | |
| 8,137,308 B2 | 3/2012 | Schultz | |
| 8,226,641 B2 | 7/2012 | Potter | |
| 8,260,399 B2 | 9/2012 | Karmarkar et al. | |
| 8,308,659 B2 | 11/2012 | Scheibe et al. | |
| 8,376,990 B2 | 2/2013 | Ponzi et al. | |
| 8,473,029 B2 | 6/2013 | Gerhart et al. | |
| 2001/0032007 A1 | 10/2001 | Hata et al. | |
| 2005/0070844 A1 | 3/2005 | Chow et al. | |
| 2006/0229700 A1 | 10/2006 | Acosta et al. | |
| 2006/0264894 A1 | 11/2006 | Moberg et al. | |
| 2007/0073098 A1 | 3/2007 | Lenker et al. | |
| 2008/0161843 A1 | 7/2008 | Clague | |
| 2008/0300571 A1 | 12/2008 | LePivert | |
| 2009/0163915 A1 | 6/2009 | Potter | |
| 2009/0171272 A1 | 7/2009 | Tegg et al. | |
| 2009/0287187 A1 | 11/2009 | Legaspi et al. | |
| 2009/0312698 A1 | 12/2009 | Farrell et al. | |
| 2010/0076408 A1 | 3/2010 | Krever et al. | |
| 2010/0168827 A1 | 7/2010 | Schultz | |
| 2010/0198049 A1 | 8/2010 | Karmarkar et al. | |
| 2010/0217261 A1 | 8/2010 | Watson | |
| 2011/0087270 A1 | 4/2011 | Penner | |
| 2011/0264074 A1 | 10/2011 | Tegg et al. | |
| 2011/0264133 A1 | 10/2011 | Hanlon et al. | |
| 2011/0282176 A1 | 11/2011 | Tegg | |
| 2012/0010490 A1 | 1/2012 | Kauphusman et al. | |
| 2012/0017923 A1 | 1/2012 | Sobe | |
| 2012/0089125 A1 | 4/2012 | Scheibe et al. | |
| 2012/0123327 A1 | 5/2012 | Miller | |
| 2012/0130218 A1 | 5/2012 | Kauphusman et al. | |
| 2012/0172717 A1 | 7/2012 | Gonda | |
| 2012/0190927 A1 | 7/2012 | Uihlein | |
| 2012/0226228 A1 | 9/2012 | Butler | |
| 2012/0277582 A1 | 11/2012 | Mafi | |
| 2012/0310212 A1 | 12/2012 | Fischell et al. | |
| 2013/0018306 A1 | 1/2013 | Ludwin | |
| 2013/0116705 A1 | 5/2013 | Salahieh et al. | |
| 2013/0165857 A1 | 6/2013 | O'Donnell et al. | |
| 2013/0165922 A1 | 6/2013 | Falwell et al. | |
| 2013/0184642 A1 | 7/2013 | O'Donnell et al. | |
| 2013/0317542 A1 | 11/2013 | Clark et al. | |
| 2014/0018732 A1 | 1/2014 | Bagaoisan et al. | |
| 2014/0100445 A1 | 4/2014 | Stenzel et al. | |

FOREIGN PATENT DOCUMENTS

| | | | |
|---|---|---|---|
| EP | 0713408 A1 | 5/1996 | |
| EP | 1676596 A1 | 5/2006 | |
| EP | 1803481 A2 | 4/2007 | |
| EP | 2116272 A1 | 11/2009 | |
| WO | WO-0117600 A1 | 3/2001 | |
| WO | WO 2007-046953 A2 | 4/2007 | |
| WO | WO 2010-082150 A1 | 7/2010 | |
| WO | WO 2011-051872 A2 | 5/2011 | |
| WO | WO 2011-055143 A1 | 5/2011 | |
| WO | WO-2012019232 A1 | 2/2012 | |
| WO | WO 2012-158263 A1 | 11/2012 | |
| WO | 2013057609 A1 | 4/2013 | |
| WO | 2013134708 A1 | 9/2013 | |

OTHER PUBLICATIONS

International Search Report and Written Opinion issued by the ISA/U.S. Receiving Office, regarding corresponding patent application Serial No. PCT/US2013/074331; dated Feb. 20, 2014; 15 pages.

International Search Report and Written Opinion issued by the ISA/U.S. Receiving Office, regarding corresponding patent application Serial No. PCT/US2012/069487; dated Feb. 26, 2013; 13 pages.

Canadian Office Action issued by the Canadian Intellectual Property Office, in regard to corresponding patent application Serial No. 2894763; dated Apr. 22, 2016; 4 pages.

(56) References Cited

OTHER PUBLICATIONS

International Search Report and Written Opinion issued by the ISA/U.S., regarding international patent application Serial No. PCT/US2015/051910, dated Dec. 18, 2015, 10 pages; USA.
International Search Report and Written Opinion issued by the ISA/U.S., regarding international patent application Serial No. PCT/US2015/050585, dated Dec. 14, 2015, 7 pages; USA.
International Search Report and Written Opinion issued by the ISA/U.S., regarding international patent application Serial No. PCT/US2015/050588, dated Dec. 17, 2015, 9 pages; USA.
Chinese Patent First Office Action issued by the State Intellectual Property Office of P.R. China, regarding corresponding patent application Serial No. 201380065624.5, dated Jun. 3, 2016, 13 pages; P.R. China—translated.

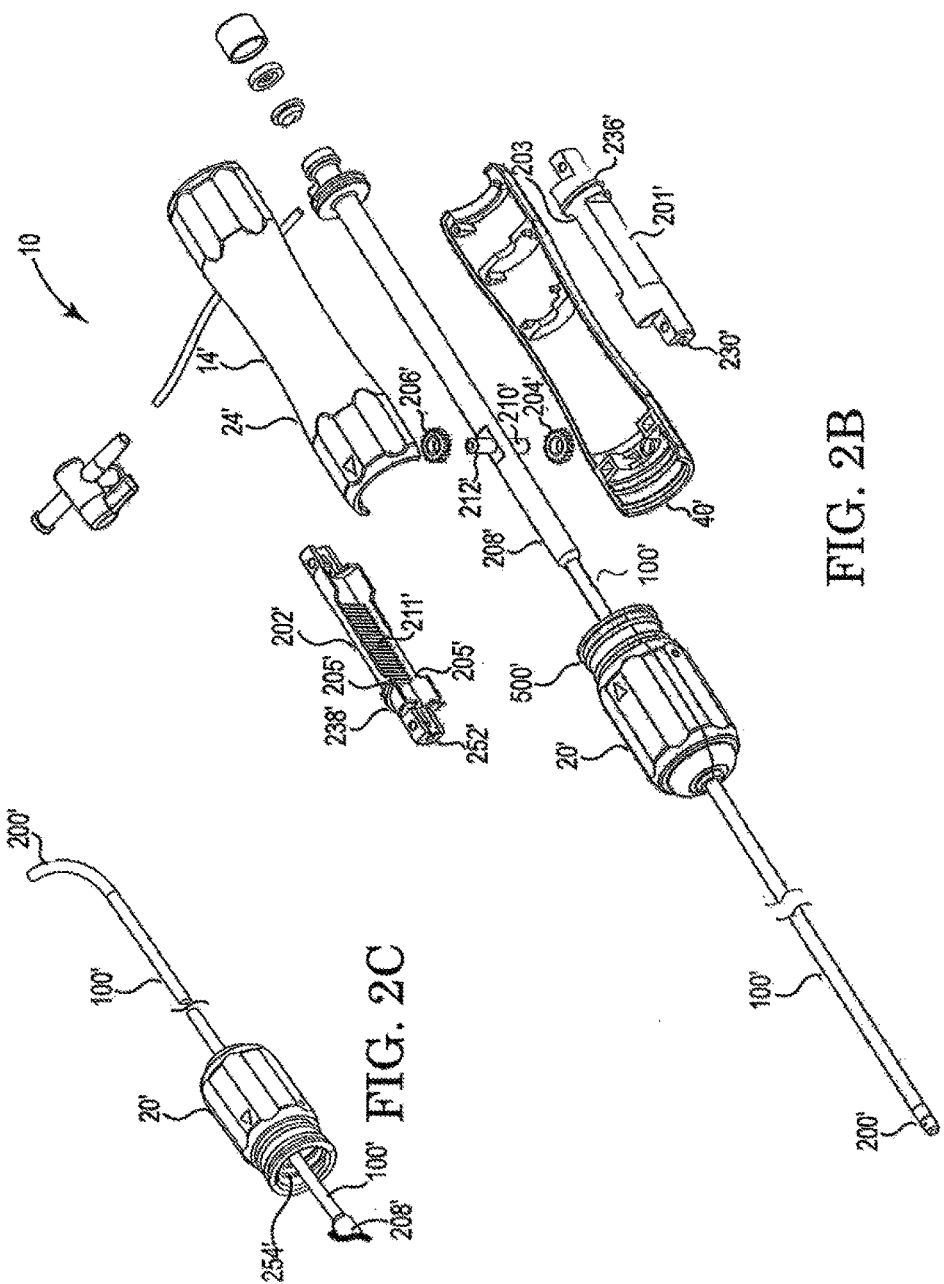

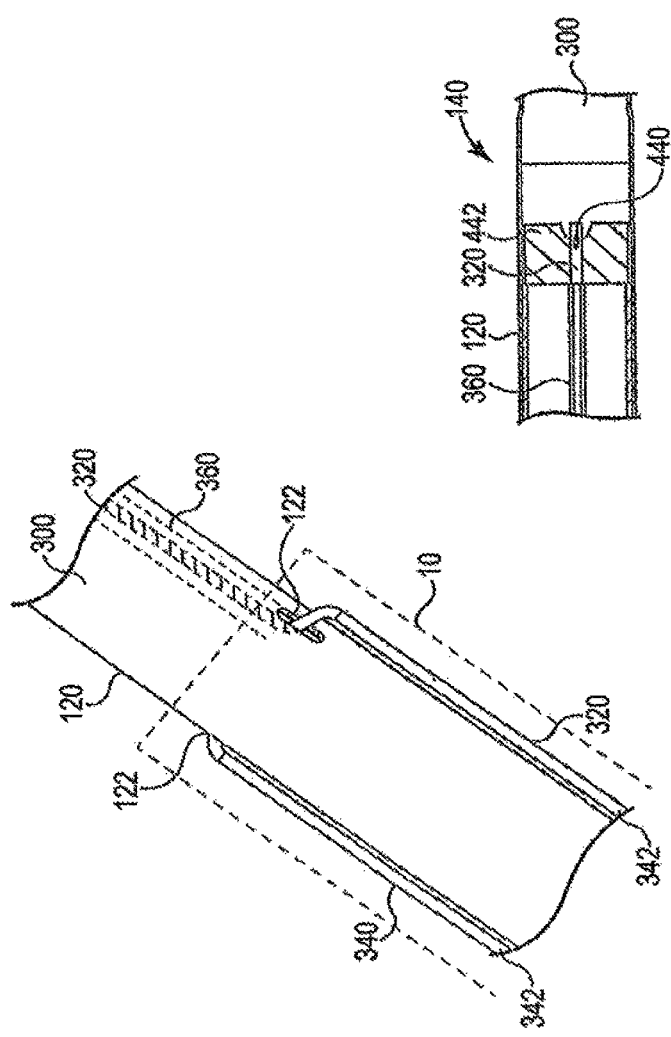

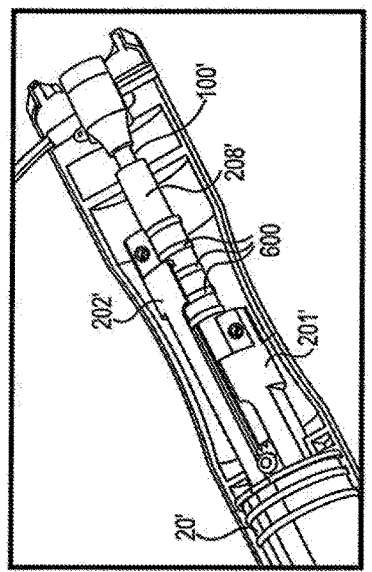
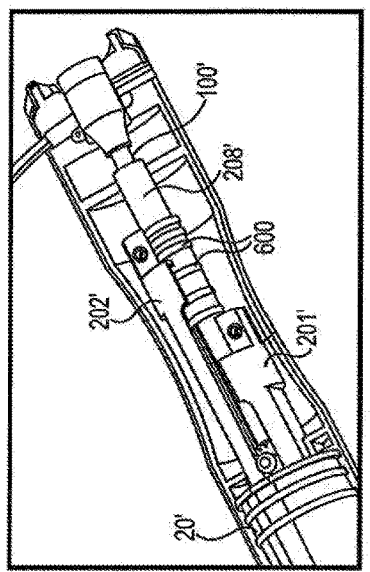

MRI COMPATIBLE CONTROL HANDLE FOR STEERABLE SHEATH WITH AUDIBLE, TACTILE AND/OR VISUAL MEANS

CROSS REFERENCE TO RELATED APPLICATIONS

This application claims the benefit of priority to U.S. Provisional application Ser. No. 62/155,100, filed on Apr. 30, 2015; and is a continuation-in-part of U.S. application Ser. No. 14/106,177, filed on Dec. 13, 2013; which is a continuation-in-part of U.S. application Ser. No. 13/819,981, filed on Feb. 28, 2013, (abandoned); which claims the benefit of PCT application Serial No.: PCT/US2012/069487, filed on Dec. 13, 2012; which claims the benefit of U.S. Provisional application Ser. No. 61/576,161, filed on Dec. 15, 2011; and U.S. application Ser. No. 14/106,177 is a continuation application of PCT application Serial No.: PCT/US2013/074331, filed on Dec. 11, 2013. The entireties of all of the foregoing are hereby incorporated by reference.

FIELD OF THE INVENTION

The present invention relates to a control handle for operating a steerable medical sheath used in interventional vascular procedures to deliver tools (e.g. electrophysiology catheters, guide wires, balloons catheters, stents, instruments, etc.) into the human body. More particularly, a control handle that includes audible, tactile and/or visual means to indicate to the user the deflection of the sheath is provided.

BACKGROUND OF THE INVENTION

Steerable medical sheaths are used in interventional vascular procedures to deliver tools (e.g. electrophysiology catheters, guide wires, balloons catheters, stents, instruments, etc.) into the human body. A control handle is necessary for operating the steerable sheath to precisely place it in the desired position. In addition, when the steerable sheath is being navigated through tortuous vessels it is desirable to be able to determine when the steerable sheath tip is in the deflection and no-deflection states.

MRI has achieved prominence as a diagnostic imaging modality, and increasingly as an interventional imaging modality. The primary benefits of MRI over other imaging modalities, such as X-ray, include superior soft tissue imaging and avoiding patient exposure to ionizing radiation produced by X-rays. MRI's superior soft tissue imaging capabilities have offered great clinical benefit with respect to diagnostic imaging. Similarly, interventional procedures, which have traditionally used X-ray imaging for guidance, stand to benefit greatly from MRI's soft tissue imaging capabilities. In addition, the significant patient exposure to ionizing radiation associated with traditional X-ray guided interventional procedures is eliminated with MRI guidance.

A variety of MRI techniques are being developed as alternatives to X-ray imaging for guiding interventional procedures. For example, as a medical device is advanced through the patient's body during an interventional procedure, its progress may be tracked so that the device can be delivered properly to a target site. Once delivered to the target site, the device and patient tissue may be monitored to improve therapy delivery. Thus, tracking the position of medical devices is useful in interventional procedures. Exemplary interventional procedures include, for example, cardiac electrophysiology procedures including diagnostic procedures for diagnosing arrhythmias and ablation procedures such as atrial fibrillation ablation, ventricular tachycardia ablation, atrial flutter ablation, Wolfe Parkinson White Syndrome ablation, AV node ablation, SVT ablations and the like. Tracking the position of medical devices using MRI is also useful in oncological procedures such as breast, liver and prostate tumor ablations; and urological procedures such as uterine fibroid and enlarged prostate ablations.

MRI uses three fields to image patient anatomy: a large static magnetic field, a time-varying magnetic gradient field, and a radiofrequency (RF) electromagnetic field. The static magnetic field and time-varying magnetic gradient field work in concert to establish both proton alignment with the static magnetic field and also spatially dependent proton spin frequencies (resonant frequencies) within the patient. The RF field, applied at the resonance frequencies, disturbs the initial alignment, such that when the protons relax back to their initial alignment, the RF emitted from the relaxation event may be detected and processed to create an image.

Each of the three fields associated with MRI presents safety risks to patients when a medical device is in close proximity to or in contact either externally or internally with patient tissue. One important safety risk is the heating that may result from an interaction between the RF field of the MRI scanner and the medical device (RF-induced heating), especially medical devices that have elongated conductive structures, such as braiding and pull-wires in catheters and sheaths.

The RF-induced heating safety risk associated with elongated metallic structures in the MRI environment results from a coupling between the RF field and the metallic structure. In this case several heating related conditions exist. One condition exists because the metallic structure electrically contacts tissue. RF currents induced in the metallic structure may be delivered into the tissue, resulting in a high current density in the tissue and associated Joule or Ohmic tissue heating. Also, RF induced currents in the metallic structure may result in increased local specific absorption of RF energy in nearby tissue, thus increasing the tissue's temperature. The foregoing phenomenon is referred to as dielectric heating. Dielectric heating may occur even if the metallic structure does not electrically contact tissue, such metallic braiding used in a steerable sheath. In addition, RF induced currents in the metallic structure may cause Ohmic heating in the structure, itself, and the resultant heat may transfer to the patient. In such cases, it is important to attempt to both reduce the RF induced current present in the metallic structure and/or eliminate it all together by eliminating the use of metal braid and long metallic pull-wires.

The static field of the MRI will cause magnetically induced displacement torque on any device containing ferromagnetic materials and has the potential to cause unwanted device movement. It is important to construct the sheath and control handle from non-magnetic materials, to eliminate the risk of unwanted device movement.

When performing interventional procedures under MRI guidance, clinical grade image quality must be maintained. Conventional steerable sheaths are not designed for the MRI and may cause image artifacts and/or distortion that significantly reduce image quality. Constructing the sheath from non-magnetic materials and eliminating all potentially resonant conductive structures allows the sheath to be used during active MR imaging without impacting image quality. Similarly, it is as important to ensure that the control handle is also constructed from non-magnetic materials thereby eliminating potentially resonant conductive structures that may prevent the control handle being used during active MR imaging.

Conventional MR compatible steerable sheaths utilize metallic braiding for torque delivery and kink resistance; metallic pull-wires and anchor bands for distal tip deflection; metallic marker bands for fluoroscopy visualization; and ferromagnetic metals in the control handle to minimize cost. Thus because the pull-wires incorporate a conductive materials they will react with the RF field of the MRI scanner and result in RF heating and the associated danger to patients and image degradation and artifacts. Additionally, conventional control handles incorporate ferromagnetic materials that may be attracted to the strong static magnetic field of the MRI scanner. Moreover, the fluoroscopy marker bands in conventional designs may not be compatible with the MR environment due to static field interactions and image degradation and, therefore, are not optimal for visibility in the MRI environment. Therefore, visualization within the MR environment may require the use of either passive or active MR tracking techniques. Passive tracking techniques include passive markers that may lead to image distortion due to direct currents or the use of inductively coupled coils. Active tracking is more robust than passive tracking but involve resonant RF coils that are attached to the device and directly connected to an MR receiver allowing for the determination of the three-dimensional coordinates of the resonant RF coils within the scanner. To the inventors' knowledge neither active nor passive tracking techniques are presently utilized in conventional steerable sheaths or control handles.

Thus, there is a need for a control handle for operating a steerable sheath that is built with MR compatible materials to eliminate the magnetic resonance environment limitations of conventional sheaths while maintaining other characteristics of conventional sheaths. Moreover, when the steerable sheath is being navigated through tortuous vessels it would be desirable to be able to determine when the steerable sheath tip is in the deflection and no-deflection states. Visual, audible and/or tactile means would thus a desirable modification to the control handle of the present invention.

BRIEF SUMMARY OF THE INVENTION

The foregoing need is addressed by the steerable sheath and control handle in accordance with the invention. In one aspect of the invention a steerable sheath is provided that may be used in an MRI environment to deliver a variety of tools (catheters, guidewires, implantable devices, etc.) into the lumens of the body. In a further aspect of the invention, the steerable sheath comprises a reinforced polymer tube in which the reinforcing material is non-metallic based (Kevlar, PEEK, Nylon, fabric, polyimide, etc.) or a hybrid of metallic and non-metallic materials and the reinforcing geometry may comprise a braid, a coil, or a slit tube that mimics a coil and combinations of the foregoing. In yet another aspect of the invention, the reinforced polymer tube may also be segmented with varying flexibility along its length to provide the user with the ability to deflect the sheath in a region in which the segment is more flexible than other segments. In yet another aspect of the invention the polymer tube may also include one or more passive visualization markers along the length of the tube and/or one or more active visualization markers along the length of the tube.

The steerable sheath in accordance with the invention also includes one or more pull-wires which are coupled with the reinforced tube and that allow the user to manipulate and deflect the polymer tube. In one aspect of the invention, the pull-wires are preferably made of a non-metallic material (Kevlar, PEEK, Nylon, fabric, etc.). One or more internal pull-wire lumens are positioned within the polymer tube construct and allow the user to manipulate the pull-wires to move smoothly during actuation. One or more anchor points connect the pull-wire in the distal portion of the polymer tube.

In another aspect of the invention a control handle on the proximal end of the reinforced tube operates longitudinal movement of the pull-wire(s). In one aspect of the invention, the handle includes paramagnetic or diamagnetic materials or combinations of paramagnetic and diamagnetic materials.

In another aspect of the invention, an MR compatible steerable sheath with audible, tactile and/or visual means is provided. The MR compatible steerable sheath includes a steerable shaft including a deflectable distal tip, the steerable shaft receiving first and second longitudinal movement wires operably coupled to the deflectable distal tip; a control handle having a main body configured to receive first and second rack screws, the second rack screw including a threaded portion on an outer surface thereof, the steerable shaft extending axially through the control handle; the first longitudinal movement wire operably coupled to the first rack screw and the second longitudinal movement operably coupled to the second rack screw; tactile, audible or visual means operably coupled to the control handle for indicating to a user the degree of deflection of the deflectable distal tip; and a rotatable adjustment knob operably engageable with the control handle, the rotatable adjustment knob solely rotatably moveable between a first position and a second position in which the internal thread is configured to engage solely the thread on the outer surface of the second rack screw, wherein the first position causes the second rack screw to move proximally in relation to the steerable shaft which in turn causes the first rack screw to move distally in relation to the steerable shaft and proximal movement of the second rack screw is configured to cause proximal longitudinal movement of the second longitudinal movement wire, and further wherein the second position is configured to move the second rack screw distally in relation to the steerable shaft which in turn causes the first rack screw to move proximally and distal movement of the second rack screw is configured to release tension on the second longitudinal movement wire, and further wherein when the second rack screw moves proximally in relation to the steerable shaft the tactile, audible or visual means provides a tactile, audible or visual indication to a user of the degree of deflection of the distal tip.

In another aspect of the MR compatible steerable sheath in accordance with the invention, the tactile, audible or visual means are removably positioned on the steerable shaft, a t-valve axle operably coupled to said steerable shaft or an inner surface of a first mating portion and a second mating portion of the control handle or may be integrally formed therewith.

In another aspect of the invention a method of using the MR compatible steerable sheath with audible, tactile and/or visual means is also provided. The method includes providing a steerable shaft defining a longitudinal axis, said steerable shaft receiving first and second longitudinal movement wires each having first and second ends, said first ends operably coupled to a distal end of said steerable shaft and said second ends operably coupled to first and second rack screws; providing a control handle having a main body configured to receive said first and second rack screws, said first and second rack screws mechanically coupled to each other by mechanical coupling means such that movement of said second rack screw along the longitudinal axis of the steerable shaft causes movement of said first rack screw in an opposite direction along the longitudinal axis of the steerable shaft, said second rack screw including a threaded portion on an outer surface at an end thereof; providing tactile, audible or visual means operably coupled to said control handle for indicating to a user the degree of deflection of the deflectable distal tip; providing a rotatable adjustment knob having an internal thread and moveable between a first position and a second position in which the internal thread is configured to engage solely the thread on the outer surface of the second rack screw; rotating said rotatable adjustment knob to said first position thereby causing engagement of the outer thread of said second rack screw such that said second rack screw moves proximally in relation to said steerable shaft and proximal movement of said second rack screw causes distal movement of said first rack screw thereby releasing tension on the first longitudinal movement wire and causes proximal longitudinal movement of the second longitudinal movement wire; rotating said rotatable adjustment knob to said second position thereby causing engagement of the outer thread of said second rack screw such that said second rack screw moves distally in relation to said steerable shaft and distal movement of said second rack screw thereby releases tension of the second longitudinal movement wire and causes said first rack screw to move proximally thereby causing proximal longitudinal movement of the first longitudinal movement wire, wherein when said second rack screw moves proximally in relation to said steerable shaft said tactile or audible means provides a tactile, audible or visual indication to a user of the degree of deflection of the distal tip.

In another aspect of the method in accordance with the invention, the tactile, audible or visual means are removably positioned on the steerable shaft, a t-valve axle operably coupled to said steerable shaft or an inner surface of a first mating portion and a second mating portion of the control handle or may be integrally formed therewith.

In yet another aspect of the invention the control handle is configured for visual, tactile and audible indicators of the deflection and no-deflection states. The indicators may include audible means such as a "popping" sound or visual means such as a gradient graphic or deflection tabs that indicate the position of the deflection.

These and other features of the invention will now be described in detail with reference to the accompanying Figures.

BRIEF DESCRIPTION OF THE DRAWINGS

For a better understanding of the invention, and to show how the same may be carried into effect, reference will now be made, by way of example, to the accompanying drawings, in which:

FIG. 2B is an exploded perspective view of the control handle and steerable sheath according to another aspect of the invention.

FIG. 2C is an enlarged view of the rotatable adjustment knob including internal threads that are circumferentially disposed about an inner wall thereof.

FIG. 5A is an enlarged view of the pull wires at the proximal end of the steerable sheath in accordance with the invention.

FIG. 5B is a detailed view of a pull ring that provides a contact point between the pull wire and the distal end of the steerable sheath in one aspect of the invention.

FIG. 14A illustrates another aspect of the control handle including a plurality of O-rings in a spaced-apart relationship along the length of the t-valve.

FIG. 14B illustrates the control handle of FIG. 14A in which the spaced-apart relationship of the O-rings decreases as the rack screw travels proximally.

DETAILED DESCRIPTION OF THE INVENTION

Figure 1:
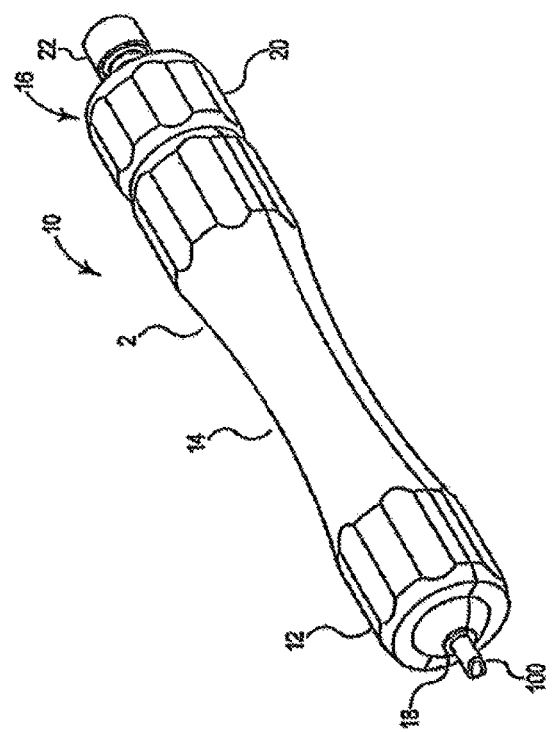
FIG. 1 is a perspective view of a control handle that may operably coupled with the steerable sheath according to an aspect of the invention.

Numerous structural variations of an MR compatible steerable sheath and control handle in accordance with the invention are contemplated and within the intended scope of the invention. Those of skill in the art will appreciate that the exemplary control handle may be coupled to other types of steerable sheaths. In addition, those of skill in the art will appreciate that the exemplary steerable sheath may be couple with other control handles. Therefore, for purposes of discussion and not limitation, an exemplary embodiment of the MR compatible steerable sheath and control handle will be described in detail below.

Referring to FIGS. 1-20 like elements have been numbered with like reference numerals.

Referring now to FIG. 1, the control handle 10 in accordance with the invention includes a cover 2 as illustrated in FIG. 1. Cover 2 includes distal portion 12, hand-graspable middle region 14, and proximal end 16. Distal portion 12 includes aperture 18 through which steerable sheath shaft 100 exits. Proximal end 16 includes rotatable adjustment knob 20 and port 22. Rotatable adjustment knob 20 is operably coupled to a proximal end (not shown) of steerable sheath shaft 100 such that rotation of the knob causes movement of steerable sheath shaft 100 as hereinafter described. Port 22 includes an aperture therethrough for receiving a medical device such as by way of example an MR-compatible electrode circuit such as that disclosed in U.S. Publn. No. 2011/0046707, the entirety of which is hereby incorporated by reference.

Figure 2A:
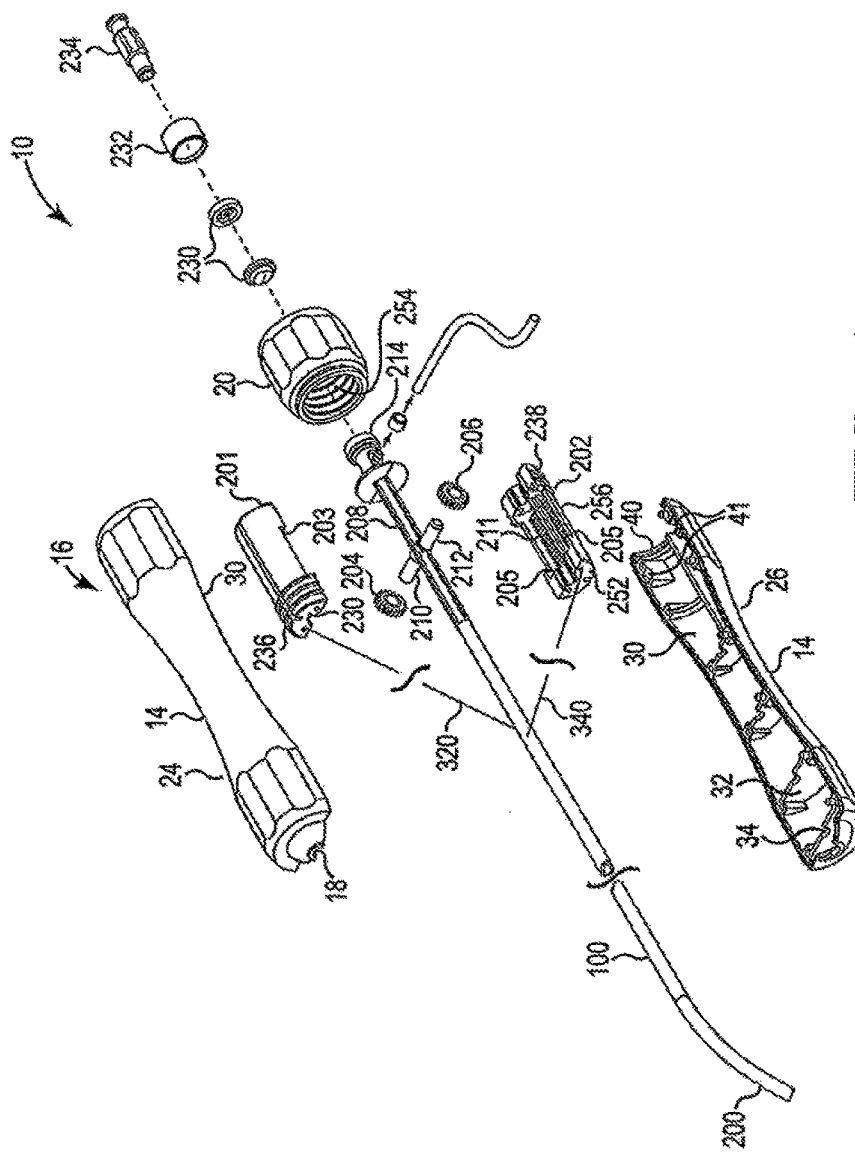
FIG. 2A is an exploded perspective view of the control handle and steerable sheath according to an aspect of the invention.

Referring now to FIG. 2A an exploded view of the control handle 10 and steerable sheath shaft 100 in accordance with the invention is shown. Cover 2 of control handle 10 includes a first mating portion 24 and a second mating portion 26. Those of skill in the art will appreciate, however, that cover 2 may include any number of mating portions and still be within the scope of the invention. Each of the first and second mating portions 24, 26 include an inner face 30 having a plurality of inserts 32 fixedly coupled to inner face 30. As depicted, inserts 32 include a receiving groove therewithin. When first mating portion and second mating portion are operably coupled, receiving groove 34 forms a lumen into which steerable sheath shaft 100 is received. First mating portion 24 and second mating portion 26 when mated form an internal recess 40 at a distal end thereof, which accommodates first and second rack screws 201, 202. It should be noted that the distal threads 236 of the first rack screw 201, although shown, have no function. First and second rack screws 201, 202 are simply mirror images of each other and the distal threads 236 of the first rack screw 201 are present to reduce the cost of manufacturing so that first and second rack screws 201, 202 can be made from the same mold. Control handle 10 further includes first and second pinion gears 204, 206, t-valve axle 208, first and second pegs 210, 212, t-valve 214, tube retainer 216, tube 218, and rotatable adjustment knob 20. Rotatable adjustment knob 20 receives seals 230, seal cap 232 and fitting 234. First and second pegs 210, 212 are operably coupled to t-valve axle 208. Groove 41 receives pegs 210, 212. First and second pegs 210, 212 receive pinion gears 204 and 206. Tube 218 attaches to a stopcock in t-valve which connects to a syringe for flushing or aspirating the steerable sheath.

As may be seen in FIG. 2A, second rack screw 202 includes proximal threads 238 on an outer surface thereof. Those of skill in the art will appreciate that "first" and "second" rack screws are relative terms. Those of skill in the art will also appreciate that the control knob 20 may be positioned distally to first and second rack screws and the orientation of first and second rack screws flipped as will be described below with reference to FIG. 2B. An internal central channel of each of first and second rack screws 201, 202 includes a threaded portion 211 that threadably receives pinion gears 204, 206 in operation. First and second rack screws 201, 202 include notched portion 203, 205. First and second pull wires 320, 340 are routed and are operably coupled to ends 230, 252 of each rack screw 201, 202, respectively. Pinion gears 204, 206 are received by pegs 210, 212 operably coupled to t-valve axle 208. T-valve axle 208 is bonded to sheath shaft 100. In operation, posts 210, 212 are received by and move longitudinally on notched portion 203, 205 respectively. This allows threaded pinion gears 204, 206 to be received by and move longitudinally along the threaded central channel of each of first and second rack screws 201, 202.

As seen in FIG. 2A, rotatable adjustment knob 20 includes internal threads 254 circumferentially disposed about an inner wall thereof. Internal threads 254 will engage the proximal threads 238 of the second rack screw 202. As the rotatable adjustment knob is rotated clock-wise the internal adjustment knob threads 254 engage the proximal threads 238 of the second rack screw 202 causing longitudinal, proximal movement of rack screw 202. As the rotatable adjustment knob is rotated counter-clockwise the internal threads (still engaged with the proximal threads 238 of the second rack screw 202) causes longitudinal, distal movement of rack screw 202.

Those of skill in the art will appreciate that the orientation of the first and second rack screws may be changed without departing from the scope of the invention. As may be seen in FIG. 2B, second rack screw 202' includes distal threads 238' on an outer surface thereof. An internal central channel of each of first and second rack screws 201', 202' includes a threaded portion 211' that threadably receives pinion gears 204', 206' in operation. First and second rack screws 201', 202' include notched portion 203', 205'. First and second pull wires (not shown) are routed and are operably coupled to ends 230', 252' of each rack screw 201', 202', respectively. Pinion gears 204', 206' are received by pegs 210', 212' operably coupled to t-valve axle 208'. T-valve axle 208' includes a lumen therewithin which slidably receives sheath shaft 100'. In operation, posts 210', 212' are received by and move longitudinally on notched portion 203', 205' respectively. This allows threaded pinion gears 204', 206' to be received by and move longitudinally along the threaded central channel of each of first and second rack screws 201', 202'.

As seen in FIG. 2C, rotatable adjustment knob 20' includes internal threads 254' circumferentially disposed about an inner wall thereof. Internal threads 254' will engage the distal threads 238' of the second rack screw 202'. As the rotatable adjustment knob 20' is rotated clock-wise the internal adjustment knob threads 254' engage the distal threads 238' of the second rack screw 202' causing longitudinal, proximal movement of rack screw 202'. As the rotatable adjustment know is rotated counter-clockwise the internal threads (still engaged with the distal threads 238' of the second rack screw 202') causes longitudinal, distal movement of rack screw 202'. Thus, those of skill in the art will appreciate that although the rotatable adjustment knob 20' is positioned distal to the first and second rack screws 201', 202' the operation of the control handle has not changed.

Figure 10:
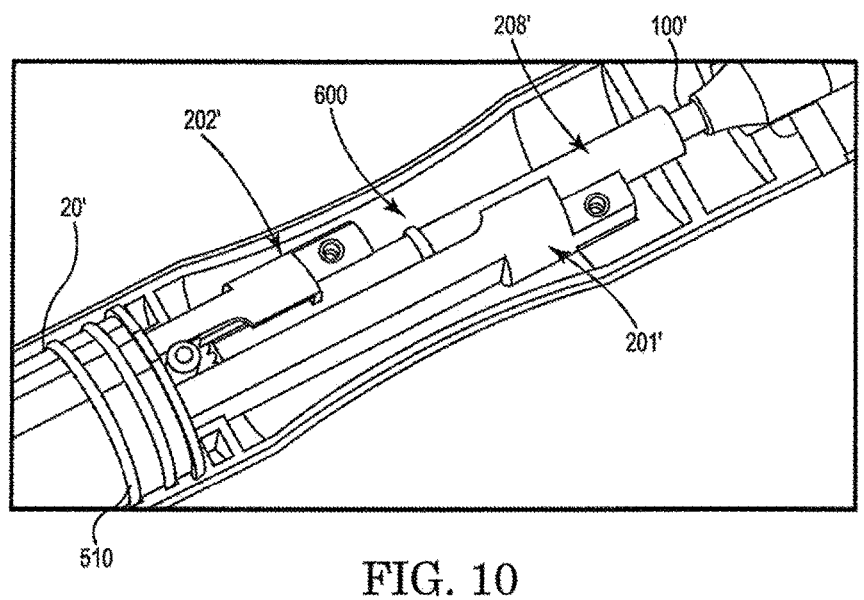
FIG. 10 is a perspective view of the control handle of FIG. 2B illustrating means for providing an audible and tactile indicator of the neutral distal "no deflection" state.

Rotatable adjustment knob 20' of FIGS. 2B and 2C includes grooves 500 on an outer surface thereof which, in operation, accommodate a plurality of O-rings 510 (as best seen in FIG. 10) that create a friction fit between the knob 20' and the first mating portion 24' and second mating portion 26' of cover 2 of control handle 10, which has corresponding grooves.

Figure 3:
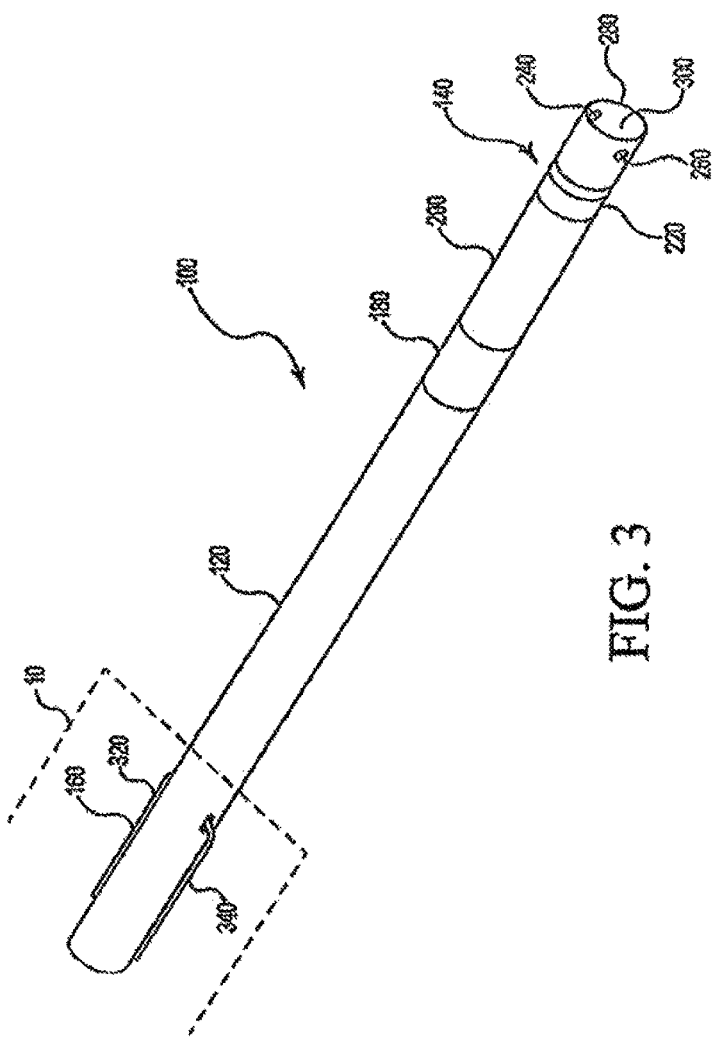
FIG. 3 is a perspective view of the steerable sheath according to an aspect of the invention.

Referring now to FIG. 3, the steerable sheath shaft 100 in accordance with the invention will now be explained. Steerable sheath shaft 100 may be used in an MRI environment to deliver a variety of tools such as catheters, guide wires, implantable devices, etc. into cavities and passageways of a patient body. The steerable sheath shaft 100 includes a deflectable tip portion 200 that is able to bend at least 180 degrees offset from the longitudinal axis of the sheath shaft 100. This flexibility allows the medical professional to make very tight turns to deliver the aforementioned tools to the cavities and passageways of the patient body.

Referring again to FIG. 3 a perspective view of an MR compatible steerable sheath that is suitable for use in an MRI environment is depicted. The MR compatible steerable sheath shaft 100 in accordance with the invention broadly includes tubular shaft 120 with distal 140 and proximal ends 160. Tubular shaft 120 includes an outer diameter 130, an inner diameter 150 and defines a central lumen 300 therewithin. Tubular shaft may be constructed of a variety of polymers such as pebax, polyurethane, nylon, derivatives thereof and combinations of the foregoing.

Distal end 14 includes transition section 180, deflectable tip portion 200, and magnetic marker 220. Pressure relief holes 240, 260 may be formed in the tubular shaft 120 at the distal end 140. Those of skill in the art will appreciate that while only two pressure relief holes 240, 260 are shown there may any number of pressure relief holes formed and still be within the scope of the invention. When retracting an item housed by the sheath shaft 100, such as a catheter or MR active tracking system, pressure may form at the end of the sheath thereby drawing or sucking in tissue. Pressure relief holes 240, 260 are designed to reduce this pressure thereby ameliorating the risk of tissue damage.

Transition section 180 is optionally included for purposes of manufacturability. The deflectable tip section 20 has a significantly lower durometer making it more malleable and flexible than the main body portion 170 of tubular shaft 120 which has a higher durometer or, in other words, quite stiff. As a consequence, these two sections do not bond to one another well. Transitional section 180 has a mid-range durometer allowing it to bond well to both the deflectable tip section 200 and the main body 170 of the tubular shaft 120. Those of skill in the art will appreciate that the transition section 180 may be of any length desired so as to provide an adequate transition between the distal tip portion 200 and the main body portion 170. In one exemplary embodiment transition section may range from about 0.25 to about 0.75 inches. In addition, those of skill in the art will appreciate that transition section may be eliminated and the deflectable tip section 200 may be coupled to the main body 170 of tubular shaft 120 by means known to those of skill in the art without departing from the spirit of the invention.

Steerable sheath shaft 100 includes central lumen 300 therewithin. In one aspect of the invention, the inner diameter 150 of the tubular shaft 120 is approximately 6 French or greater but those of skill in the art will appreciate that varying internal diameters may be used depending on the particular application without departing from the scope of the present invention. Central lumen 300 may include one or more liners (not shown) disposed therewithin to allow for easier movement of instruments therethrough. Liners may comprise materials made from polytetrafluoroethylene (PTFE), fluorinated ethylene propylene copolymer (FEP), nylons and combinations of the foregoing. Alternatively, the lumen 300 may be coated with any such polymers. The polymer tubular shaft 120 may also include one or more passive visualization markers, such as a ferrous or magnetic marker 220, disposed circumferentially about the tubular shaft 120 at one or more locations along the length thereof and/or one or more active visualization markers such as an active tracking coil along the length of the tube. An active tracking coil may comprise one or more small antennas integrated into the device and include traces on a circuit board, coiled wire, and/or a dipole. If an active visualization marker is used, one or more devices may be included in the conductors to mitigate RF field heating may be included. Such devices include chokes, transformers, impedances, and other such devices known to those of skill in the art. One or more fluoroscopy markers (not shown) may also be included along the length of the polymer tubular shaft 12.

One or more optional fluid ports (not shown) may be located on the proximal end 16 of the tubular shaft 12 to allow for homeostasis of the sheath with the patient body. The fluid port(s) allows access for the user or physician to aspirate blood from the steerable sheath lumen 30 and flush with saline. Aspirating and flushing of the sheath prevents air from entering the body before and during insertion of a tool and/or catheter.

Figure 4:
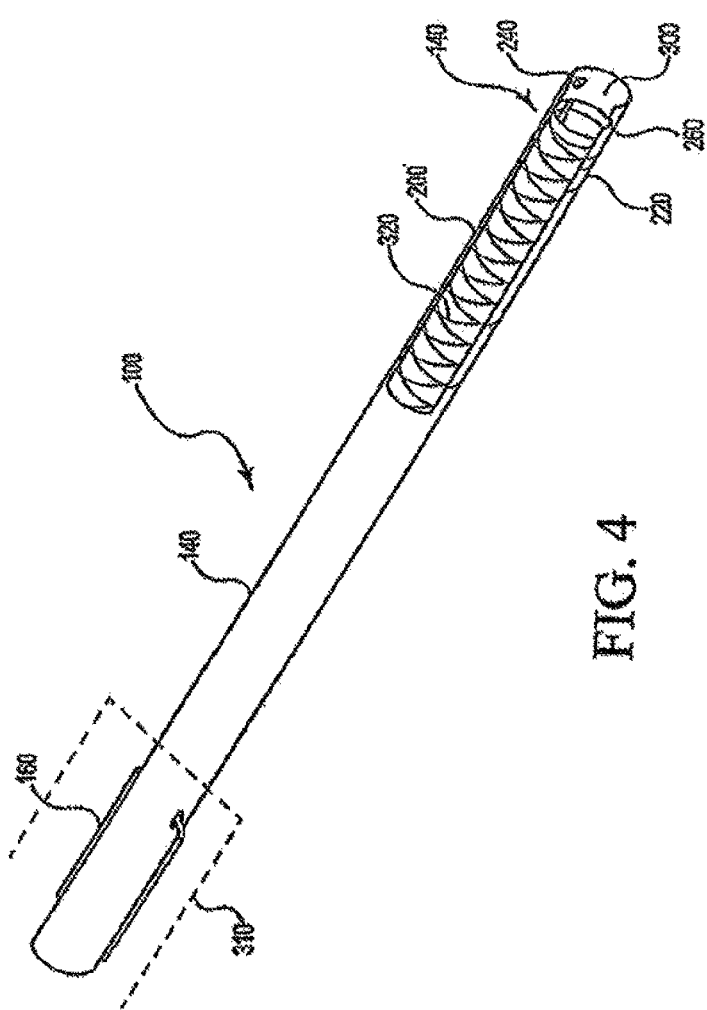
FIG. 4 is a perspective view of the steerable sheath according to an aspect of the invention with the steerable distal tip cut away to show detail.

Referring now to FIG. 4 a cut away view of the steerable sheath shaft 100 in accordance with the invention depicts a reinforcement construct 320 of the tubular shaft 120. As shown, the geometry of the reinforcement construct 320 is braided but those of skill in the art will appreciate that the reinforcement construct 320 may comprise other configurations so long as it imparts the necessary deflectability to the tubular shaft 120 at the distal end. For example the reinforcement geometry may be a coil or a slit tube that mimics a coil or combinations of the foregoing. The reinforcement of the tubular shaft 120 may extend from the distal end 140 to the proximal end 160 or may extend from the deflectable tip section 200 to approximately the transition section 180 of the tubular shaft 12.

The material used in the reinforcement construct 320 may be non-metallic such as Kevlar, PEEK, Nylon, fabric, polyimide, fiber optic, silica glass and the like or may also be hybrid of metallic, such as stainless steel, and non-metallic materials. Those of skill in the art will appreciate that, the reinforced polymer tubular shaft 140 may be segmented and each segment may be constructed with varying flexibility along the segment to provide the user with the ability to deflect the sheath in a region in which the segment is more flexible than in other segments. Varying flexibility and thus deflectability may be accomplished by having braids or coils that have greater braiding or coils per sq. cm than in other segments where the braiding or coiling would be less per sq. cm. Flexibility and deflectability may also be accomplished by the varying durometers as herein described.

Referring now to FIG. 5A, an enlarged view of the proximal end 160 of the steerable sheath shaft 100 in accordance with the invention is depicted. Proximal end 160 of the steerable sheath is operably coupled to control handle 10 depicted in dashed lines and as hereinafter described. The steerable sheath shaft 100 in accordance with the invention includes one or more pull-wires 320, 340 which are operably coupled at a pull-wire proximal end 342 to the control handle 10 as hereinafter will be described. The portion of the pull-wires 320, 340 that are operably coupled to the control handle exit the tubular body 120 at opening 122. The portion of the pull-wires 320, 340 that are operably coupled to pull ring 440 (as best seen in FIG. 5B) extend through a lumen constructed from a sheet of polymeric material fastened to an inner portion of tubular shaft 120 for a length thereof and enter tubular shaft 120 through entrance holes 330, 350 on opposing sides of tubular shaft 120. Pull-wires 320, 340 allow the user to manipulate and deflect the one or more flexible segments along the length of the polymer tubular shaft 120 and in particular the deflectable tip portion 200. In one aspect of the invention, the pull-wires 320, 340 are preferably made of a non-metallic material (Kevlar, PEEK, Nylon, fabric, etc.).

One or more internal pull-wire lumens 360 are constructed of a flexible, non-metallic material such as PTFE. Internal pull-wire lumens 360 facilitate smooth manipulation of the pull-wires 320, 340 during actuation. Internal pull-wire lumens 360 have an outer diameter of approximately 0.12 inches and an inner diameter of approximately 0.010 inches. However, those of skill in the art will appreciate that the dimensions of the internal pull-wire lumens 360 may vary with the dimensions of both the pull-wires 320, 340 and the tubular shaft 120 so long as they are dimensioned to house the pull-wires and allow pull-wires to move smoothly during actuation.

Referring to FIG. 5B, a side view of the distal end of the steerable sheath in accordance with the invention is shown. Pull wires 320, 340 are operably coupled at their distal end to an opening 440 in pull ring 442 positioned within lumen 300 at the deflectable tip 200 end of the steerable sheath shaft 100.

Referring now to FIGS. 6-9 an exemplary control handle 31 for operating the steerable sheath is disclosed. As discussed in reference to FIG. 2, control handle 310 allows the user to control the longitudinal movement of pull-wires 320, 340 which in turn "pull" or deflect the distal end 140 of the steerable sheath shaft 100 in opposite directions. Control handle 310 is positioned on the proximal end of the steerable sheath shaft 100 and operates longitudinal movement of the pull-wire(s) and correspondingly, directional movement of the steerable sheath shaft 100. In one aspect of the invention, control handle 310 includes paramagnetic or diamagnetic materials or combinations of paramagnetic and diamagnetic materials.

Figure 6A:
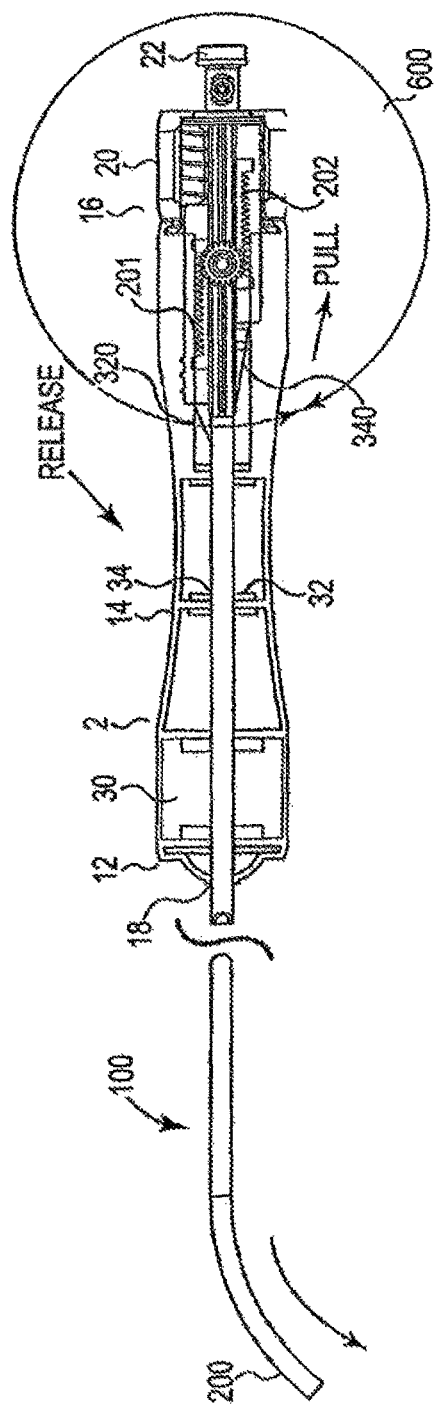
FIG. 6A is a side view of the control handle and steerable sheath of FIG. 2A.
Figure 6B:
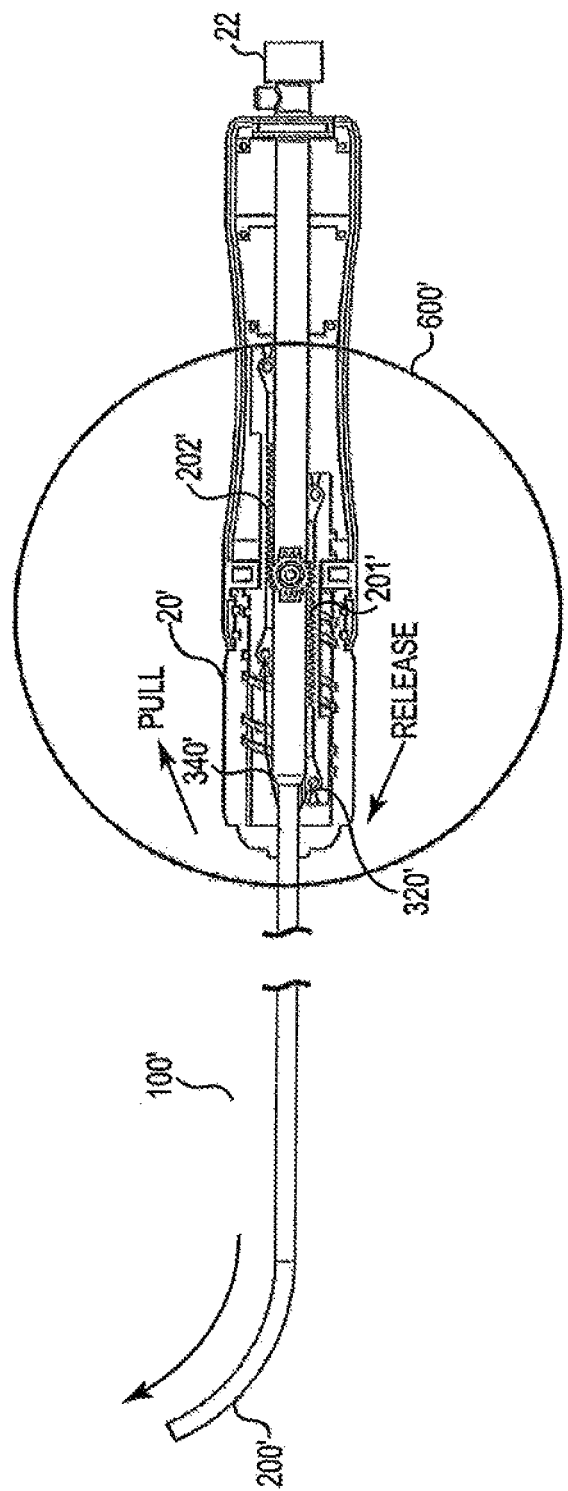
FIG. 6B is a side view of the control handle and steerable sheath of FIG. 2B.
Figure 7A:
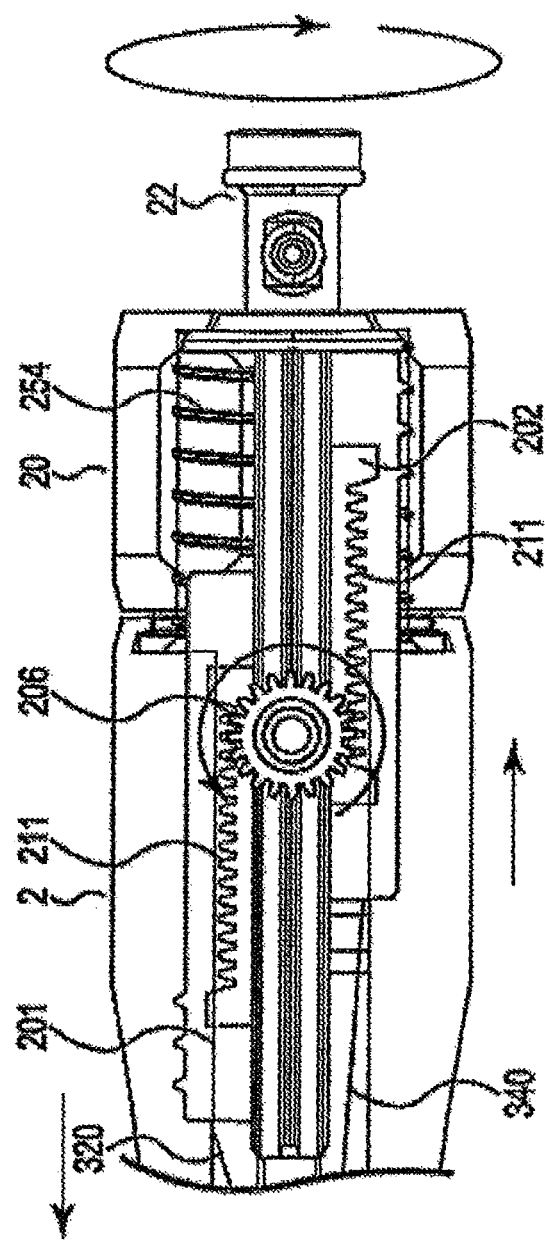
FIG. 7A is an enlarged view of the control handle mechanical structure denoted by 600 in FIG. 6A and showing clockwise rotation of rotatable knob.
Figure 7B:
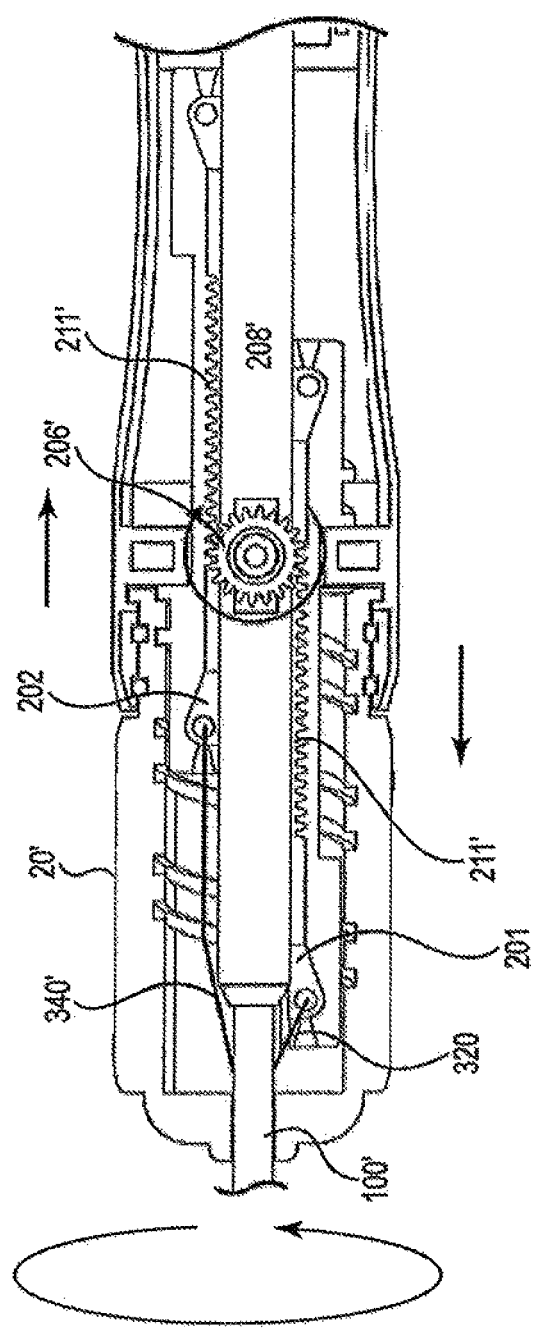
FIG. 7B is an enlarged view of the control handle mechanical structure denoted by 600' in FIG. 6B and showing clockwise rotation of rotatable knob.
Figure 8A:
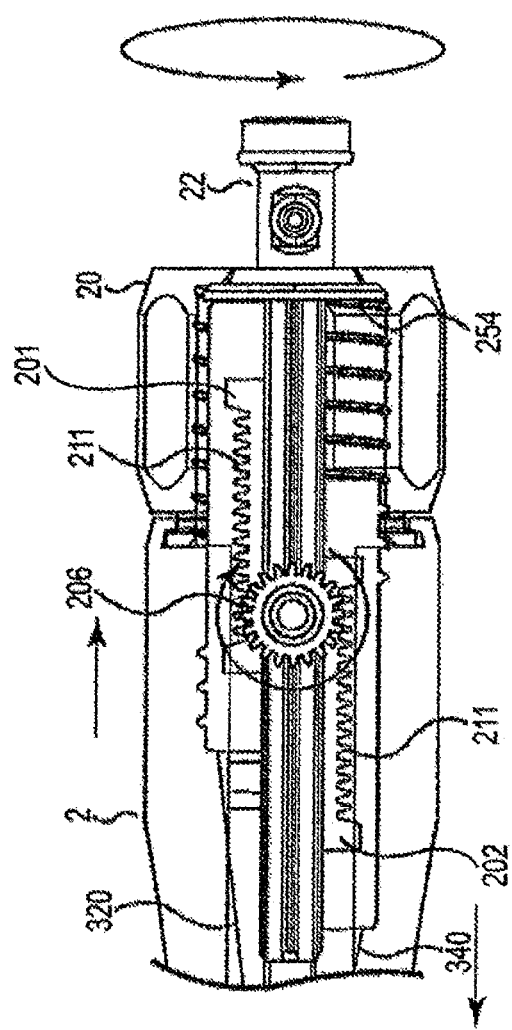
FIG. 8A is an enlarged view of the control handle mechanical structure denoted by 800 in FIG. 6A and showing counterclockwise rotation of rotatable knob.
Figure 8B:
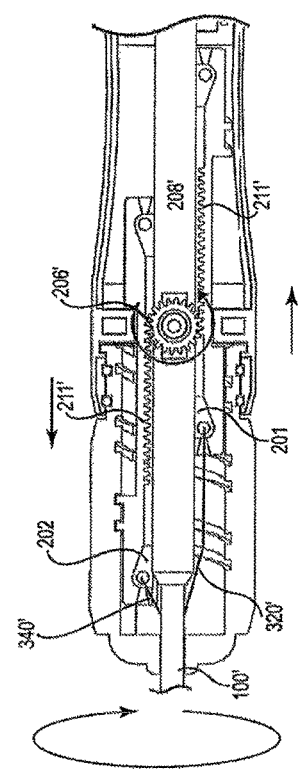
FIG. 8B is an enlarged view of the control handle mechanical structure denoted by 800' in FIG. 6B and showing counterclockwise rotation of rotatable knob.

Referring now to FIGS. 6A-7B, FIGS. 7A and 7B are enlarged views of the control handle of FIGS. 6A and 6B denoted at numeral 600, 600'. Adjustment knob 20, 20' is rotated in the clockwise direction, which causes internal threads 254, 254' to engage threads 238, 238' of second rack screw 202, 202' and cause longitudinal, proximal movement of the second rack screw 202, 202'. At the same time, the pinion gears are engaged by the longitudinal movement of the second rack screw 202, 202'. This causes the first rack screw 201, 201' to move in the opposite direction, i.e. distally. Distal movement of the first rack screw 201, 201' releases tension in the first pull wire 320, 320'.

As rotatable adjustment knob 20, 20' is rotated in the clockwise direction and engages rack screws which in turn engage pinion gears, second pull wire 340, 340' is pulled toward the proximal direction as best seen in FIGS. 6A and 6B. In turn, the tension on first pull wire 320, 320' is released. As second pull wire 340, 340' is pulled in the proximal direction deflectable tip moves in one direction, shown as a downward direction in FIG. 6A and an upward direction in FIG. 6B; however those of skill in the art will appreciate that the direction of deflectable tip is relative to how or the direction in which the user is holding the handle 10. When the t-valve pegs 210, 210', 212, 212' abut stops 205, 205' in second rack screw 202, 202' the rack screw 202, 202' stops moving and further movement of rotatable adjustment knob 20, 20' is halted.

Referring now to FIGS. 8A, 8B and 9A, 9B the opposite function is illustrated. Adjustment knob 20, 20' is rotated in the counter-clockwise direction, internal threads 254, 254' engage threads 238, 238' of second rack screw 202, 202' causing longitudinal, distal movement.

Figure 9A:
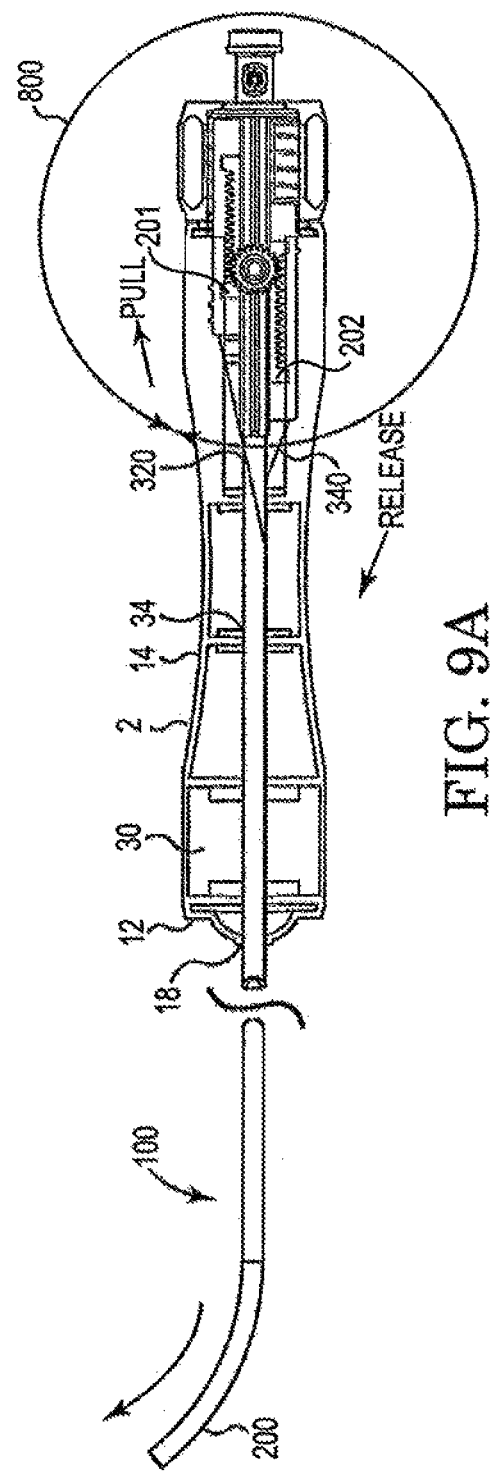
FIG. 9A is a side view of the control handle of FIG. 2A showing the function of the pull wire.
Figure 9B:
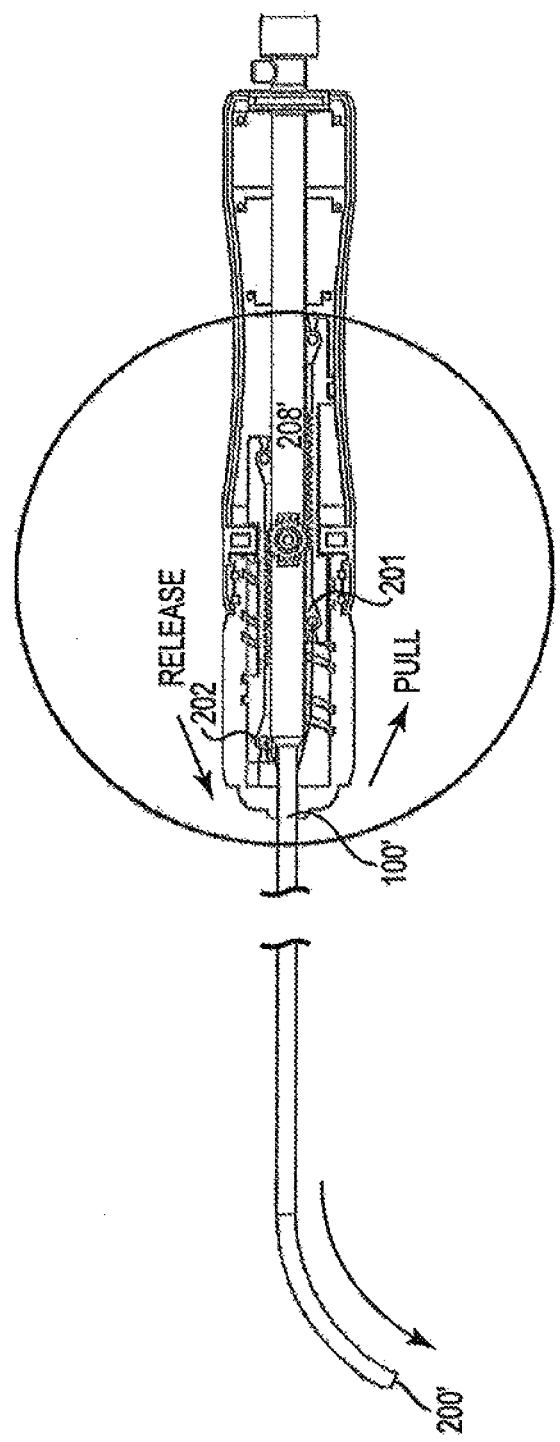
FIG. 9B is a side view of the control handle of FIG. 2B showing the function of the pull wire.

As rotatable adjustment knob 20, 20' is rotated in the counter-clockwise direction first pull wire 320, 320' is pulled toward the proximal direction as best seen in FIGS. 9A and 9B. In turn, the tension on second pull wire 340, 340' is released. As first pull wire 320, 320' is pulled in the proximal direction deflectable tip moves in the opposite direction, shown as an upward direction in FIG. 9A and a downward direction in FIG. 9B; however those of skill in the art will appreciate that the direction of deflectable tip is relative to how, or the direction in which, the user is holding the handle 10. When the t-valve pegs 210, 210', 212, 212' abut stops 205, 205' in second rack screw 202, 202' the rack screw 202, 202' stops moving and further movement of rotatable adjustment knob 20, 20' is halted.

Referring now to FIGS. 10-20, the control handle of FIGS. 1-9B has been modified to include a tactile and/or audible indicator of the neutral distal curve or the "no-deflection" state of the steerable sheath tip 200 in accordance with the invention. An exemplary embodiment will use control handle 10' to describe the invention. When navigating through tortuous vessels it is important for the user to be able to determine when the steerable sheath tip is in the no-deflection state. Audible and tactile means are thus a desirable modification to the control handle of the present invention.

FIG. 10 shows the control handle 10' in accordance with the invention having a tactile and audible indicator of the neutral distal curve (no deflection) state. A rubber or other suitable material O-ring 600 is positioned on the t-valve shaft 208' such that first and second rack screws 201', 202' have to slide over the O-ring 600 in order to move proximally or distally. If the linear position of the O-ring 600 on the t-valve shaft 208' corresponds to the position in which the first and second rack screws 201', 202' are aligned, the engagement of the O-ring 600 occurs at the point in which the curve of the distal tip 200' is straight (as best seen in FIG. 2B) and is thus an indicator of the neutral curve position. Because the O-ring 600 is rubber or other suitable material, when the rack screws 201', 202' engage and travel over the O-ring 600, there is a moment of slight resistance that must be overcome. This resistance is transferred to the rotatable adjustment knob 20' and the user perceives this as a rotary, tactile indication of the neutral position. In addition, when the first and second rack screws 201', 202' engage and travel over the O-ring 600, there is also an audible 'pop' or 'snap', which functions as the audible indicator of the neutral position. Those of skill in the art will appreciate that the audible/tactile means in accordance with the invention could also be positioned on the steerable shaft 100', the t-valve axle 208' or on an inner surface of first mating portion 24 and second mating portion 26 of cover 2 of control handle 10.

Figure 11:
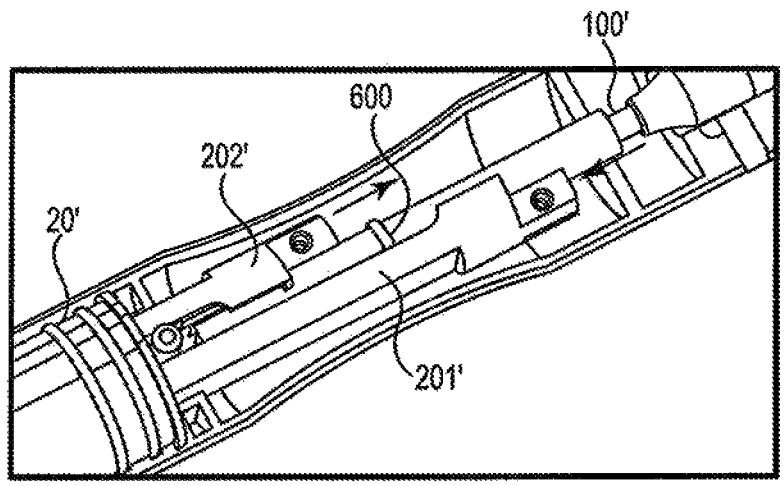
FIG. 11 is the control handle of FIG. 10 showing the movement of the two rack screws as they approach alignment.

FIG. 11 illustrates first and second rack screws 201', 202' approaching the position in which they are aligned.

Figure 12:
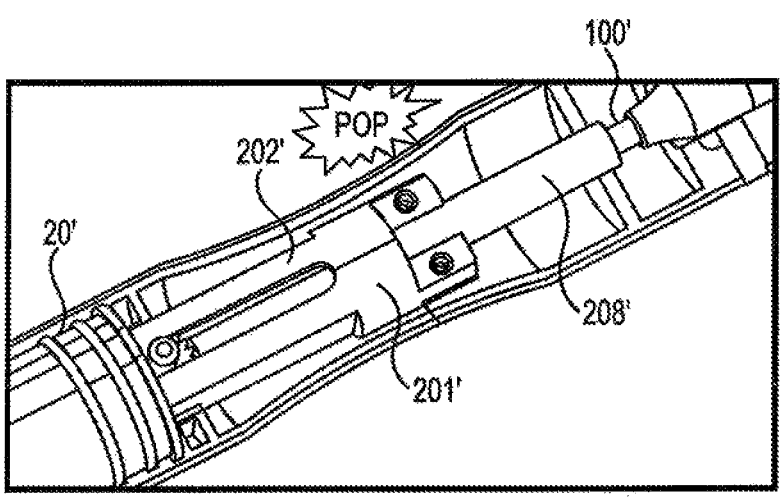
FIG. 12 illustrates an audible signal to the user as the rack screws become aligned.

FIG. 12 depicts the first and second rack screws 201', 202' in alignment. In order to be in the aligned position, the first and second rack screws 201', 202' must overcome the O-ring 600. When they do so there is an audible pop and a moment of resistance that the user feels in the rotatable adjustment knob 20'.

Figure 13:
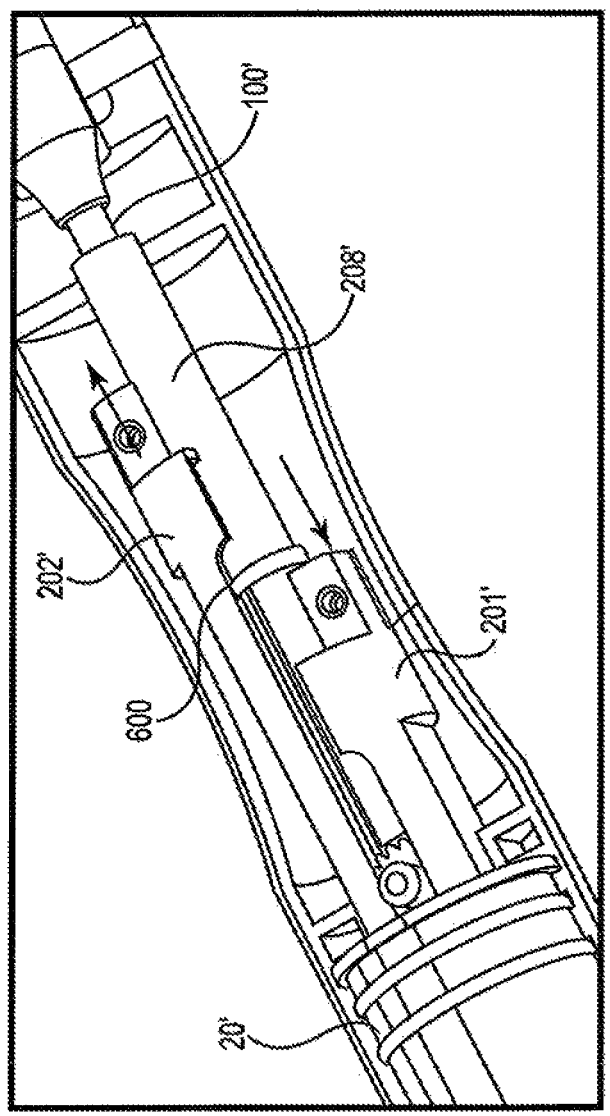
FIG. 13 illustrates the rack screws moving past the position of alignment.

Referring now to FIG. 13, first and second rack screws 201' 202' have moved past the position of alignment and over the O-ring 600. If the rotatable adjustment knob 20' is rotated in the opposite direction, clock-wise or counter-clockwise, the rack screws 201', 202' will again move linearly towards each other and the position of alignment, which corresponds to the neutral curve position, and the O-ring 600 must be overcome again.

The O-ring 600 of the control handle 10' may be removably positioned in a groove in the t-valve shaft 208' or the O-ring 600 may be molded into the t-valve shaft 208'.

Referring now to FIGS. 14A and 14B other aspects of the control handle are shown. A plurality of O-rings 600 are positioned in a spaced-apart relationship along the outer diameter of the t-valve shaft 208' along a length thereof. The spacing between the O-Rings may be positioned such that they correspond with degrees of deflection of the curve of the distal tip 200'. For example, FIG. 14A depicts that the spaced-apart relationship of the O-rings 600 may be substantially equidistant such that they indicate a repeating degree of curve deflection, such as every 15 degrees of curve deflection. Of course, those of skill in the art will appreciate that other angle increments could be indicated, such as every 30 degrees of deflection.

In another aspect, as best seen in FIG. 14B, the spacing of a plurality of O-rings 600 is such that the distance between them varies. The spacing of the O-rings in the proximal direction decreases as the deflection curve approaches the maximum deflection. In this case, the user feels and hears more pops as the curve approaches maximum deflection. This is a method of indicating the degree of curve deflection without the user having to understand or remember how much angular deflection corresponds with each knob 'pop'. In another aspect FIG. 14B illustrates that the spacing between the O-rings 600 is variable. As shown, the spacing between O-rings 600 increases in the proximal direction. Those of skill in the art will appreciate, however, that other spacing permutations are within the scope of the invention. For example, the spacing may be close together in the middle and then further apart proximally in which case the user would feel and hear fewer tactile and audible signals, respectively, as the rack screw moved proximally and the sheath tip is correspondingly deflected. Those of skill in the art will also appreciate that the O-rings 600 may be located on the proximal aspect of the t-valve axle 208' of the distal aspect or both.

Figure 15:
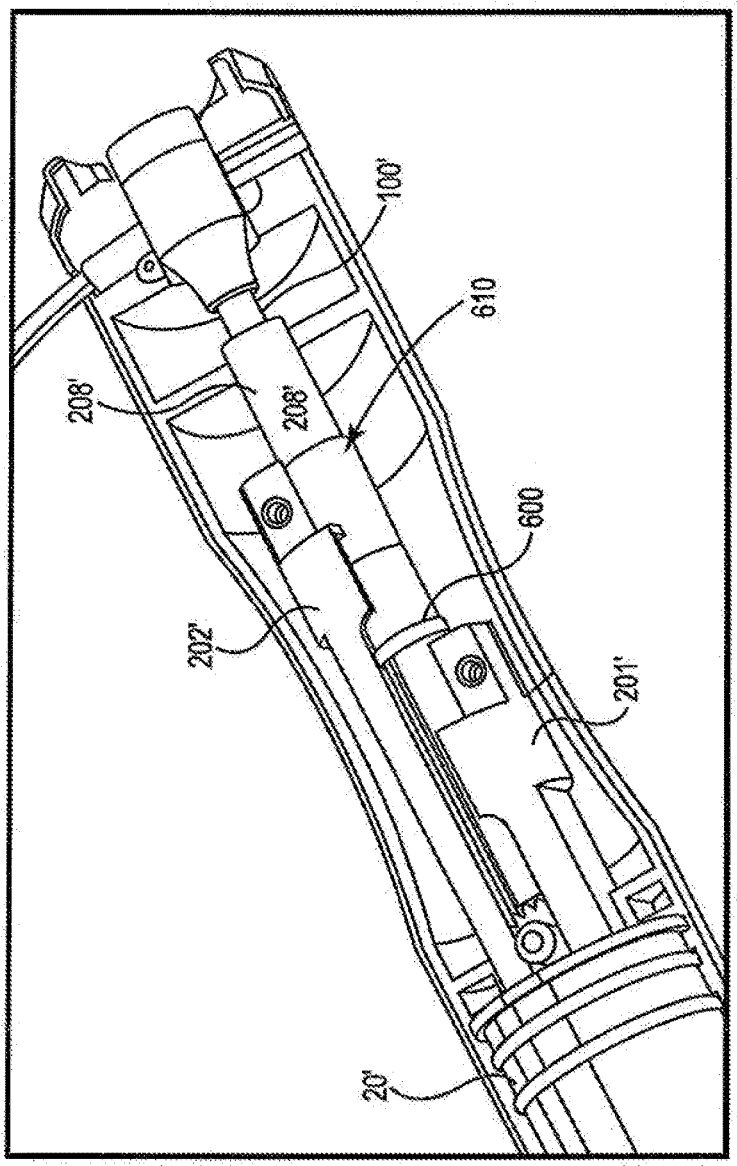
FIG. 15 illustrates another aspect of the control handle including a ramp proximate the distal end of the t-valve

Referring now to FIG. 15 the t-valve shaft 208' may also include an integral or non-integral ramp 610 positioned at the distal end of the shaft 208'. Ramp 610 may be used alone or together with one or more O-rings 600. Ramp 610 provides a gradually increasing resistance as the first and second rack screws 201', 202' move proximally. A corresponding increasing rotational resistance of the rotatable adjustment knob 20' may be felt by the user as the curve of deflection approaches maximal deflection. The increasing rotational resistance indicates to the user that the curve of the deflection tip 200' is increasing towards the point of maximum deflection. As the first and second rack screws 201', 202' engage and travel across ramp 610, an increasing rotational resistance is felt within the knob 20', which corresponds to increasing distal tip curve deflection and is a tactile means for indicating to the user that the curve deflection is gradually increasing toward the point of maximal deflection.

Figure 16:
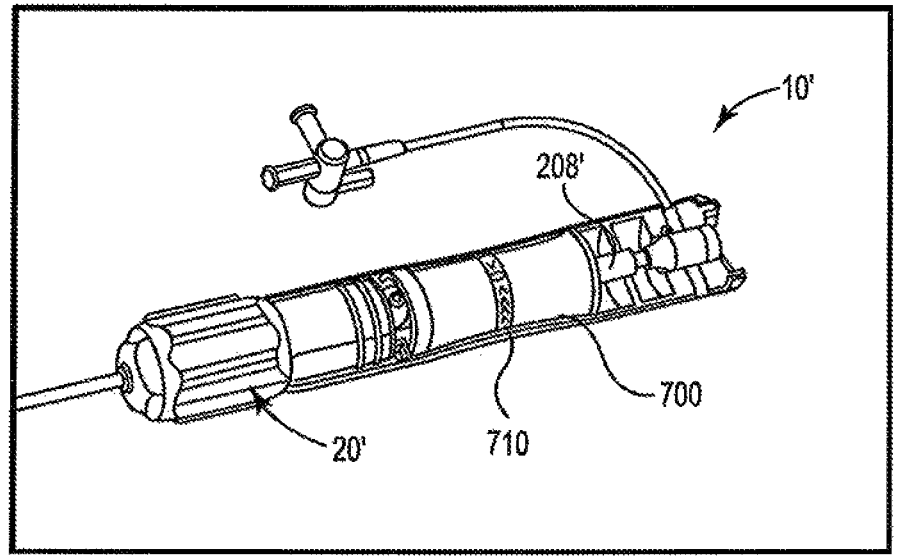
FIG. 16 illustrates another aspect of the control handle including an angle knob positioned within the handle.

Referring now to FIG. 16, another aspect of the control handle 10' in accordance with the invention is shown. In this embodiment an 'angle knob' 700 is positioned within the control handle 10'. Angle knob 700 includes threads (not shown) on an inner surface thereof that threadingly interface with threads 236' on the proximal surface of first rack screw 201'. Thus, travel of the first rack screw 201' along a linear path in turn causes rotation of the angle knob 700.

Figure 17:
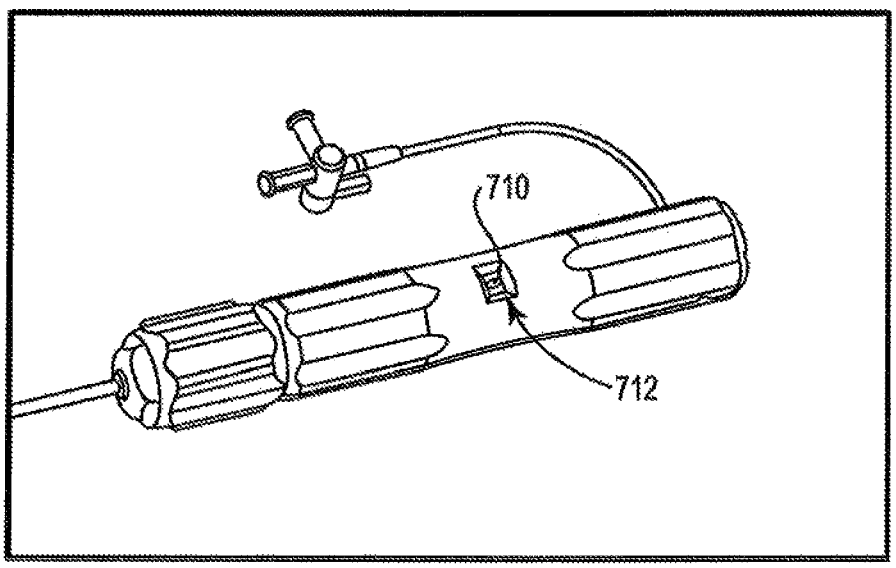
FIG. 17 illustrates a window through which the angle of rotation is visible to the user.

The threads 236' of the first rack screw 201' may optionally have a different pitch than the threads 238' on the distal surface of the second rack screw 202. Those of skill in the art will appreciate that one advantage of this feature is that the angle knob 700 would rotate at a different rate than the rotatable adjustment knob 20' being turned by the user. Thus, if the design requires that the rotatable adjustment knob 20' has to be turned multiple times to achieve maximum distal tip sheath deflection, the angle knob 700 may be turned 180 degrees in one direction and 180 degrees in the opposite direction thereby indicating the exact or approximate deflection of the distal tip 200', which deflects at least 180 degrees, but less than 360 degrees, in opposing directions. In other words, the rotatable adjustment knob 20' is not capable of having any indication of distal tip curve deflection if it is rotated by more than 360 degrees in a clockwise or counterclockwise direction because the distal tip sheath 200' deflects at least approximately 180 degrees, but less than 360 degrees. In addition, having the angle knob 700 only rotate 180 degrees in either direction allows the depiction of curve deflection direction. Therefore, the user can look at the angle knob and instantly understand to what degree the curve is deflected and in which direction. In addition, angle knob angle indicators 710 may be positioned on the outer diameter of the angle knob 700 and the control handle 10' would have a small window 712 therein allowing the rotation angle to be visible to the user as best seen in FIG. 17.

Figure 18:
FIG. 18 illustrates another aspect of the invention in which a gradient graphic is used on the angle knob.

In yet further aspects of the invention, the graphics on the angle knob may be a visual gradient 714 as best seen in FIG. 18. This would impart a qualitative picture of sheath tip 200 angle deflection to the user without having to be as precise as angle deflections numbers 710. Those of skill in the art will appreciate that the gradient 714 depicted in FIG. 18 is illustrative and not limiting as many other types of gradients may be employed.

Figure 19:
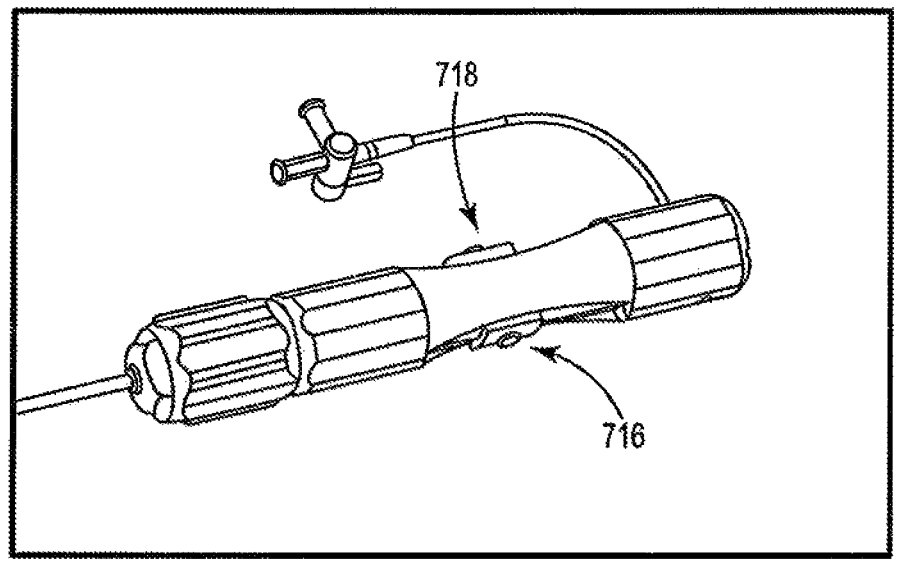
FIG. 19 illustrates another aspect of the invention in which the control handle includes deflection tabs thereon (shown in the neutral position) each of which operably couples to one rack screw.

Referring now to FIG. 19, the rack screws include first and second deflection tabs 716, 718 are positioned on the outer surface of control handle 10' and are operably coupled to first 201' and second 202' rack screws respectively. Depending on the position of the rack screw and its corresponding deflection tab 716, 718 the user may feel and visually determine the state of the distal tip 200 curve deflection. By way of example, when tabs 716, 718 are substantially aligned, the user would understand that the distal tip 200' curve is in the neutral, "no-deflection" state. When the first deflection tab 716 is in the end proximal position, the user would understand that the distal tip 200' was fully deflected to the same side as the first deflection tab 716. When the second deflection tab 718 is in its end proximal position, the user would understand that the distal tip 200' is fully deflected to the same side as the second deflection tab 718.

Figure 20:
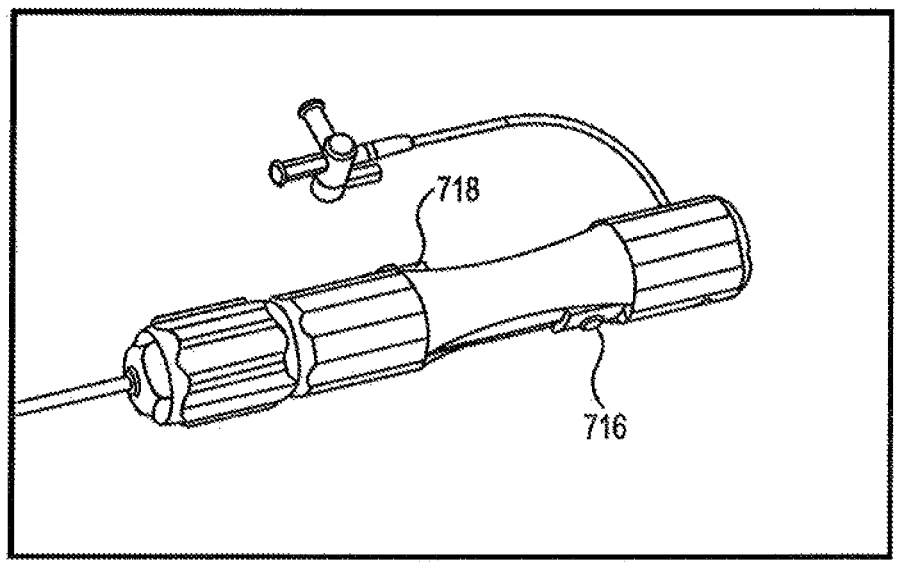
FIG. 20 shows the control handle of FIG. 19 in which one of the deflection tabs is in the proximal position indicating that the distal tip has been fully deflected in the direction of that tab.

Deflection tabs are configured to correspond to the amount of distal curve deflection. As best seen in FIG. 19 the deflection tabs 716, 718 are substantially aligned, indicating to the user that the distal curve is in the neutral, no deflection state. As seen in FIG. 20 the first deflection tab 716 has moved to the end proximal position indicating to the user that the distal tip 200 curve is fully deflected in the direction of the first tab 716.

Although the present invention has been described with reference to preferred embodiments, workers skilled in the art will recognize that changes may be made in form and detail without departing from the spirit and scope of the invention.

We claim:

1. An MR compatible steerable sheath comprising:
   a steerable shaft including a deflectable distal tip, said steerable shaft receiving first and second longitudinal movement wires operably coupled to said deflectable distal tip;
   a control handle having a main body configured to receive first and second rack screws, said second rack screw including a threaded portion on an outer surface thereof, said steerable shaft extending axially through said control handle;
   said first longitudinal movement wire operably coupled to said first rack screw and said second longitudinal movement operably coupled to said second rack screw;
   tactile, audible or visual means operably coupled to said control handle for indicating to a user the degree of deflection of the deflectable distal tip; and
   a rotatable adjustment knob operably engageable with said control handle, said rotatable adjustment knob solely rotatably moveable between a first position and a second position in which the internal thread is configured to engage solely the thread on the outer surface of said second rack screw,
   wherein said first position causes said second rack screw to move proximally in relation to said steerable shaft which in turn causes said first rack screw to move distally in relation to said steerable shaft and proximal movement of said second rack screw is configured to cause proximal longitudinal movement of the second longitudinal movement wire,
   and further wherein said second position is configured to move said second rack screw distally in relation to said steerable shaft which in turn causes said first rack screw to move proximally and distal movement of said second rack screw is configured to release tension on the second longitudinal movement wire,
   and further wherein when said second rack screw moves proximally in relation to said steerable shaft said tactile, audible or visual means provides a tactile, audible or visual indication to a user of the degree of deflection of the distal tip.

2. The MR compatible steerable sheath of claim 1 wherein said proximal longitudinal movement of said second longitudinal movement wire causes the distal end of said steerable shaft to deflect from 180 degrees to less than 360 degrees from a longitudinal axis of the steerable shaft in a first direction.

3. The MR compatible steerable sheath of claim 1 wherein said tactile or audible means comprise at least one O-ring positioned on either the steerable shaft, a t-valve axle operably coupled to said steerable shaft or on an inner surface of a first mating portion and second mating portion of the control handle.

4. The MR compatible steerable sheath of claim 3 wherein said at least one O-ring may be removably positioned on either the steerable shaft, said t-valve axle operably coupled to said steerable shaft or the inner surface of the first mating portion and second mating portion of the control handle or may be integrally formed therewith.

5. The MR compatible steerable sheath of claim 3 wherein said O-rings comprise a plurality of O-rings spaced apart in an equidistant relationship.

6. The MR compatible steerable sheath of claim 3 wherein said O-rings comprise a plurality of O-rings spaced apart in a varying relationship.

7. The MR compatible steerable sheath of claim 5 wherein said plurality of O-rings are configured to provide a tactile means to a user by increasing the rotational resistance of the control knob as the deflectable distal tip approximates full deflection.

8. The MR compatible steerable sheath of claim 4 wherein said at least one O-ring is configured to received said first and second rack screws and provide an audible means to a user by emitting an audible sound to a user as the first and second rack screws are received by said one or more O-rings.

9. The MR compatible steerable sheath of claim 1 wherein said tactile, audible or visual means includes an angle knob positioned on said control handle for visually indicating to a user the degree and angle of deflection of said distal tip.

10. The MR compatible steerable sheath of claim 9 wherein said angle knob is positioned on a t-valve axle operably coupled to said steerable sheath.

11. The MR compatible steerable sheath of claim 9 wherein said angle knob includes numerals thereon for visually indicating to a user the degree and angle of deflection of said distal tip.

12. The MR compatible steerable sheath of claim 9 further including a window on said control handle for viewing said visual means.

13. The MR compatible steerable sheath of claim 9 wherein said angle knob includes a gradient thereon for visually indicating to a user the degree and angle of deflection of said distal tip.

14. The MR compatible steerable sheath of claim 1 wherein said tactile, audible or visual means includes first and second deflection tabs operably coupled to said first and second rack screws, respectively and positioned on an outer surface of said control handle.

15. The MR compatible steerable sheath of claim 14 wherein when said first and second deflection tabs are substantially aligned a visual indication is provided to the user that the curve of the distal tip is in the neutral, no deflection state.

16. The MR compatible steerable sheath of claim 14, wherein when the first deflection tab is at the end proximal position a visual indication is provided to the user that the curve of the distal tip is fully deflected in the direction of the first deflection tab.

17. The MR compatible steerable sheath of claim 14, wherein when the second deflection tab is at the end proximal position a visual indication is provided to the user that the curve of the distal tip is fully deflected in the direction of the second deflection tab.

18. The MR compatible steerable sheath of claim 9 wherein said angle knob threadingly engages proximal threads on said first rack screw.

19. The MR compatible steerable sheath of claim 9 wherein said first rack screw includes threads on a proximal end thereof and said second rack screw includes threads on a distal end thereof, said first and second rack screw threads having a different pitch.

20. The MR compatible steerable sheath of claim 9 wherein said first rack screw includes threads on a proximal end thereof and said second rack screw includes threads on a distal end thereof, said first and second rack screw threads having the same pitch.

21. The MR compatible steerable sheath of claim 1 wherein said first rack screw includes threads on a proximal end thereof and said second rack screw includes threads on a distal end thereof.

22. A method of using an MR compatible steerable sheath having audible, tactile or visual means comprising:
   providing a steerable shaft defining a longitudinal axis, said steerable shaft receiving first and second longitudinal movement wires each having first and second ends, said first ends operably coupled to a distal end of said steerable shaft and said second ends operably coupled to first and second rack screws;
   providing a control handle having a main body configured to receive said first and second rack screws, said first and second rack screws mechanically coupled to each other by mechanical coupling means such that movement of said second rack screw along the longitudinal axis of the steerable shaft causes movement of said first rack screw in an opposite direction along the longitudinal axis of the steerable shaft, said second rack screw including a threaded portion on an outer surface at an end thereof;
   providing tactile, audible or visual means operably coupled to said control handle for indicating to a user the degree of deflection of the deflectable distal tip;
   providing a rotatable adjustment knob having an internal thread and moveable between a first position and a second position in which the internal thread is configured to engage solely the thread on the outer surface of the second rack screw;
   rotating said rotatable adjustment knob to said first position thereby causing engagement of the outer thread of said second rack screw such that said second rack screw moves proximally in relation to said steerable shaft and proximal movement of said second rack screw causes distal movement of said first rack screw thereby releasing tension on the first longitudinal movement wire and causes proximal longitudinal movement of the second longitudinal movement wire;
   rotating said rotatable adjustment knob to said second position thereby causing engagement of the outer thread of said second rack screw such that said second rack screw moves distally in relation to said steerable shaft and distal movement of said second rack screw thereby releases tension of the second longitudinal movement wire and causes said first rack screw to move proximally thereby causing proximal longitudinal movement of the first longitudinal movement wire, wherein when said second rack screw moves proximally in relation to said steerable shaft said tactile or audible means provides a tactile, audible or visual indication to a user of the degree of deflection of the distal tip.

23. The MR compatible steerable sheath of claim 22 wherein said tactile, audible or visual means are removably positioned on the steerable shaft, a t-valve axle operably coupled to said steerable shaft or an inner surface of a first mating portion and a second mating portion of the control handle or may be integrally formed therewith.

* * * * *